US011354125B2

(12) United States Patent
Teng et al.

(10) Patent No.: US 11,354,125 B2
(45) Date of Patent: Jun. 7, 2022

(54) SYSTEMS AND METHODS FOR PROCESSING AN IMAGE

(71) Applicant: SHANGHAI UNITED IMAGING HEALTHCARE CO., LTD., Shanghai (CN)

(72) Inventors: Wanli Teng, Shanghai (CN); Yecheng Han, Shanghai (CN); Yong E, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/914,279

(22) Filed: Jun. 27, 2020

(65) Prior Publication Data
US 2020/0326943 A1 Oct. 15, 2020

Related U.S. Application Data

(63) Continuation of application No. PCT/CN2018/122267, filed on Dec. 20, 2018.

(30) Foreign Application Priority Data

Dec. 27, 2017 (CN) .......................... 201711446172.1

(51) Int. Cl.
*G06F 9/44* (2018.01)
*G06F 9/30* (2018.01)
(Continued)

(52) U.S. Cl.
CPC ........ *G06F 9/30036* (2013.01); *G06F 9/3001* (2013.01); *G06T 1/20* (2013.01); *G16H 30/40* (2018.01)

(58) Field of Classification Search
CPC ...... G06F 9/30036; G06F 9/3001; G06T 1/20
See application file for complete search history.

(56) References Cited

U.S. PATENT DOCUMENTS 7,825,936 B1* 11/2010 Bastos ...................... G06T 1/20
345/582
9,342,374 B2* 5/2016 Shows ................... G06F 9/5088
(Continued)

FOREIGN PATENT DOCUMENTS

CN 104331858 A 2/2015
CN 105787910 A 7/2016
(Continued)

OTHER PUBLICATIONS

Marvin Damschen et al., Timing Analysis of Tasks on Runtime Reconfigurable Processors, IEEE Transactions On Very Large Scale Integration (VLSI) Systems, 25(1): 294-307, 2017.
(Continued)

*Primary Examiner* — Cheng Yuan Tseng
(74) *Attorney, Agent, or Firm* — Metis IP LLC

(57) ABSTRACT

A method for processing a medical image is provided. The method may include obtaining the medical image, and processing the medical image using a processing program. The processing program may include one or more optimized computation units. The one or more optimized computation units may be optimized by an instruction set supported by the at least one CPU. The instruction set may be configured to optimize at least one of an operation time of the processing program, a resource of the at least one CPU occupied by the processing program, and a count of instructions included in the processing program.

20 Claims, 11 Drawing Sheets

(51) Int. Cl.
*G16H 30/40* (2018.01)
*G06T 1/20* (2006.01)

(56) References Cited

U.S. PATENT DOCUMENTS

| | | |
|---|---|---|
| 10,147,181 B2 * | 12/2018 | Nitta .................. G06T 5/10 |
| 2014/0173608 A1 | 6/2014 | Jeong |
| 2017/0206068 A1 * | 7/2017 | Johnson ............ G06F 8/443 |

FOREIGN PATENT DOCUMENTS

| | | |
|---|---|---|
| WO | 2010051167 A1 | 5/2010 |
| WO | 2019128828 A1 | 7/2019 |

OTHER PUBLICATIONS

Unmesh D. Bordoloi et al., Customizing Instruction Set Extensible Reconfigurable Processors using GPUs, 2012 25th International Conference On VLSI Design, 418-423, 2012.
The Extended European Search Report in European Application No. 18896354.0 dated Feb. 3, 2021, 8 pages.
International Search Report in PCT/CN2018/122267 dated Mar. 19, 2019, 4 pages.
Written Opinion in PCT/CN2018/122267 dated Mar. 19, 2019, 5 pages.

* cited by examiner

SYSTEMS AND METHODS FOR PROCESSING AN IMAGE

CROSS-REFERENCE TO RELATED APPLICATIONS

This application is a continuation of International Application No. PCT/CN2018/122267 field on Dec. 20, 2018, which claims priority to Chinese Application No. 201711446172.1, filed on Dec. 27, 2017, the contents of each of which are hereby incorporated by reference.

TECHNICAL FIELD

The present disclosure generally relates to systems and methods for image processing, and more specifically, relates to systems and methods for processing an image using optimized computation units.

BACKGROUND

With the development of medical technology, the demand for high-resolution medical images is becoming more and more urgent. High-resolution medical images can help doctors make more accurate diagnoses of patients' diseases. However, as the resolution of medical images increases, the difficulty of the processing of the medical images is increasing. Accurate diagnose of diseases relies on fast and accurate processing of medical images. Conventionally, a graphics processing unit (GPU) is used to perform image processing on medical images. However, GPU(s) may occupy a certain amount of space of a workstation associated with a medical device. In addition, the high cost of high-performance GPU(s) may lead to an increase in the cost of the medical device. Thus, it is desirable to provide systems and methods for processing a medical image more efficiently.

SUMMARY

In one aspect of the present disclosure, a method for processing a medical image is provided. The method may include: obtaining the medical image; and/or processing the medical image using a processing program. The processing program may include one or more optimized computation units. The one or more optimized computation units may be optimized by an instruction set supported by the at least one CPU. The instruction set may be configured to optimize at least one of: an operation time of the processing program, a resource of the at least one CPU occupied by the processing program, and a count of instructions included in the processing program.

In some embodiments, the instruction set may include at least one of an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, or a virtual machine extension (VMX) instruction set.

In some embodiments, the at least one CPU may include at least two cores corresponding to at least two threads respectively. Processing the medical image using a processing program may include: processing the medical image by implementing the processing program using the at least two threads.

In some embodiments, the medical image may be generated by a single modality imaging device or a multi-modality imaging device.

In some embodiments, the single modality imaging device may include a CT imaging device, an MR imaging device, a PET imaging device, a CBCT imaging device, an SPET imaging device, an XR imaging device, an FFDM imaging device, or a DBT imaging device.

In some embodiments, the multi-modality imaging device may include a PET-MR imaging device, a PET-CT imaging device, or an SPET-CT imaging device.

In another aspect of the present disclosure, a method for processing an image is provided. The method may include: obtaining an image; and processing the image using a processing program. The processing program may include one or more optimized computation units. The one or more optimized computation units may be obtained according to a process. The process may include: obtaining a plurality of initial computation units of the processing program, each of the plurality of initial computation units having at least one type of parameter indicating at least one operational performance of the each of the plurality of initial computation units, each of the at least one type of parameter for each of the plurality of initial computation units having a parameter value; determining at least one instruction set that the at least one CPU supports; determining a parameter value of the at least one type of parameter for each of the plurality of initial computation units; and generating the one or more optimized computation units by optimizing one or more initial computation units of the plurality of initial computation units using the at least one instruction set, based on the plurality of parameter values of a specific type of parameter for the plurality of initial computation units.

In some embodiments, the instruction set includes at least one of an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, or a virtual machine extension (VMX) instruction set.

In some embodiments, the at least one type of parameter indicating at least one operational performance of the each of the plurality of initial computation units may include an operation time of the each of the plurality of initial computation units.

In some embodiments, the method may further include: determining a ranking of the plurality of initial computation units based on the plurality of parameter values of the specific type of parameter for the plurality of initial computation units.

In some embodiments, the determining a ranking of the plurality of initial computation units may include: ranking the plurality of initial computation units according to their operation times in a descending order.

In some embodiments, generating the one or more optimized computation units by optimizing one or more initial computation units of the plurality of initial computation units using the at least one instruction set may include: generating the one or more optimized computation units by optimizing one or more initial computation units of the plurality of initial computation units using the at least one instruction set and according to the ranking of the plurality of initial computation units.

In some embodiments, the generating the one or more optimized computation units may include: determining an expected total operation time of the processing program; selecting the one or more initial computation units from the plurality of initial computation units based on the expected total operation time and the operation time associated with each of the plurality of initial computation units, according to the ranking of the plurality of initial computation units; and optimizing the one or more initial computation units using the at least one instruction set.

In some embodiments, the generating the one or more optimized computation units may include: determining an expected total operation time of the processing program; after optimizing each initial computation unit of the one or more initial computation units, determining an estimated total operation time of the processing program based on the operation times associated with the one or more optimized computation units and the rest of the plurality of initial computation units; and determining whether the estimated total operation time is less than or equal to the expected total operation time.

In some embodiments, the generating the one or more optimized computation units may further include: upon determination that the estimated total operation time is less than or equal to the expected total operation time, terminating the optimization of the one or more initial computation units.

In some embodiments, the generating the one or more optimized computation units may further include: upon determination that the estimated total operation time is larger than the expected total operation time, determining whether the optimizing operation has been performed on all of the plurality of initial computation units.

In some embodiments, the generating the one or more optimized computation units may further include: upon determination that the optimizing operation has been performed on all of the plurality of initial computation units, generating, in the processing program, an instruction for adding one or more threads for processing the image in the at least one CPU, or invoking multi threads for processing the image in the at least one CPU.

In some embodiments, the at least one type of parameter indicating at least one operational performance of the each of the plurality of initial computation units may include multiple types of parameters.

In some embodiments, the multiple types of parameters indicating the operational performances of the each of the plurality of initial computation units may include two or more of an operation time of the each of the plurality of initial computation units, a resource of the at least one CPU occupied by the each of the plurality of initial computation units, and a count of instructions included in the each of the plurality of initial computation units.

In some embodiments, the determining a ranking of the plurality of initial computation units may include: for each of the plurality of initial computation units, determining a score for each type of the multiple types of parameters associated with the each of the plurality of initial computation units; and determining a total score for the each of the plurality of initial computation units based on the score for the each type of the multiple types of parameters associated with the each of the plurality of initial computation units; and determining the ranking of the plurality of initial computation units based on the total scores of the plurality of initial computation units.

In some embodiments, the determining a score for each type of the multiple types of parameters associated with the each of the plurality of initial computation units may include: for the each type of the multiple types of parameters, determining the score for the each type associated with the each of the plurality of initial computation units by normalizing the plurality of parameter values of the each type associated with the plurality of initial computation units.

In some embodiments, the determining a total score for the each of the plurality of initial computation units may include: determining the total score for the each of the plurality of initial computation units based on a weighted mean of the scores for the multiple types of parameters associated with the each of the plurality of initial computation units.

In another aspect of the present disclosure, a system for processing a medical image is provided. The system may include: at least one storage device including a set of instructions or programs; and at least one central processing unit (CPU) configured to communicate with the at least one storage device, wherein when executing the set of instructions or programs, the at least one CPU is configured to cause the system to perform operations including: obtaining the medical image; and processing the medical image using a processing program, the processing program including one or more optimized computation units, wherein the one or more optimized computation units are optimized by an instruction set supported by the at least one CPU, the instruction set being configured to optimize at least one of: an operation time of the processing program, a resource of the at least one CPU occupied by the processing program, and a count of instructions included in the processing program.

In another aspect of the present disclosure, a system for processing an image is provided. The system may include: at least one storage device including a set of instructions or programs; and at least one central processing unit (CPU) configured to communicate with the at least one storage device, wherein when executing the set of instructions or programs, the at least one CPU is configured to cause the system to perform operations including: obtaining an image; and processing the image using a processing program, the processing program including one or more optimized computation units. The one or more optimized computation units may be obtained according to a process. The process may include: obtaining a plurality of initial computation units of the processing program, each of the plurality of initial computation units having at least one type of parameter indicating at least one operational performance of the each of the plurality of initial computation units, each of the at least one type of parameter for each of the plurality of initial computation units having a parameter value; determining at least one instruction set that the at least one CPU supports; determining a parameter value of the at least one type of parameter for each of the plurality of initial computation units; and generating the one or more optimized computation units by optimizing one or more initial computation units of the plurality of initial computation units using the at least one instruction set, based on the plurality of parameter values of a specific type of parameter for the plurality of initial computation units.

In another aspect of the present disclosure, a system for processing a medical image is provided. The system may include: an obtaining unit configured to obtain the medical image; and a processing unit configured to process the medical image using a processing program, the processing program including one or more optimized computation units, wherein the one or more optimized computation units are optimized by an instruction set supported by the at least one CPU, the instruction set being configured to optimize at least one of: an operation time of the processing program, a resource of the at least one CPU occupied by the processing program, and a count of instructions included in the processing program.

In another aspect of the present disclosure, a system for processing an image is provided. The system may include: an obtaining unit configured to obtain an image; and a processing unit configured to process the image using a processing program, the processing program including one or more optimized computation units. The one or more optimized computation units may be obtained according to a process. The process may include: obtaining a plurality of initial computation units of the processing program, each of the plurality of initial computation units having at least one type of parameter indicating at least one operational performance of the each of the plurality of initial computation units, each of the at least one type of parameter for each of the plurality of initial computation units having a parameter value; determining at least one instruction set that the at least one CPU supports; determining a parameter value of the at least one type of parameter for each of the plurality of initial computation units; and generating the one or more optimized computation units by optimizing one or more initial computation units of the plurality of initial computation units using the at least one instruction set, based on the plurality of parameter values of a specific type of parameter for the plurality of initial computation units.

In another aspect of the present disclosure, a non-transitory computer readable medium is provided. The non-transitory computer readable medium may store instructions, the instructions, when executed by at least one central processing unit (CPU), causing the at least one CPU to implement a method comprising: obtaining the medical image; and processing the medical image using a processing program, the processing program including one or more optimized computation units, wherein the one or more optimized computation units are optimized by an instruction set supported by the at least one CPU, the instruction set being configured to optimize at least one of: an operation time of the processing program, a resource of the at least one CPU occupied by the processing program, and a count of instructions included in the processing program.

In another aspect of the present disclosure, a non-transitory computer readable medium is provided. The non-transitory computer readable medium may store instructions, the instructions, when executed by at least one central processing unit (CPU), causing the at least one CPU to implement a method comprising: obtaining an image; and processing the image using a processing program, the processing program including one or more optimized computation units. The one or more optimized computation units may be obtained according to a process. The process may include: obtaining a plurality of initial computation units of the processing program, each of the plurality of initial computation units having at least one type of parameter indicating at least one operational performance of the each of the plurality of initial computation units, each of the at least one type of parameter for each of the plurality of initial computation units having a parameter value; determining at least one instruction set that the at least one CPU supports; determining a parameter value of the at least one type of parameter for each of the plurality of initial computation units; and generating the one or more optimized computation units by optimizing one or more initial computation units of the plurality of initial computation units using the at least one instruction set, based on the plurality of parameter values of a specific type of parameter for the plurality of initial computation units.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
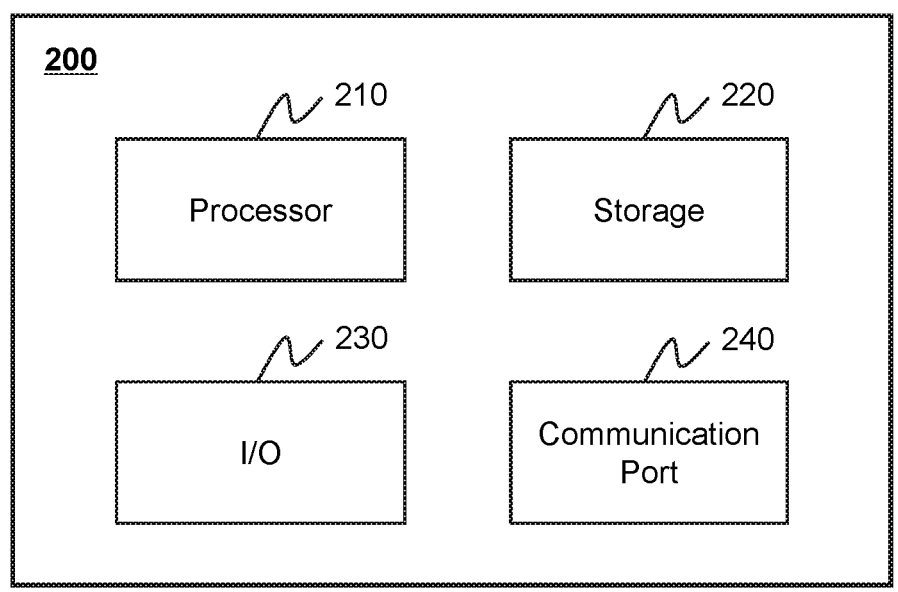
FIG. 2 is a schematic diagram illustrating an exemplary computing device on which at least a portion of the image processing system can be implemented, according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for processing an image. The systems and the methods may obtain an image, and process the image using a processing program. The processing program may include one or more optimized computation units. In order to determine the one or more optimized computation units, the systems and methods may obtain a plurality of initial computation units of the processing program. Each of the plurality of initial computation units may have at least one type of parameter indicating at least one operational performance of the each of the plurality of initial computation units. Each of the at least one type of parameters for each of the plurality of initial computation units may have a parameter value. The systems and methods may also determine at least one instruction set that at least one processor (e.g., a central processing unit (CPU)) supports. The systems and methods may also determine a parameter value of the at least one type of parameter for each of the plurality of initial computation units. The systems and methods may further determine a ranking of the plurality of initial computation units based on the plurality of parameter values of a specific type of parameter for the plurality of initial computation units. The systems and methods may still further generate the one or more optimized computation units by optimizing one or more initial computation units of the plurality of initial computation units using the at least one instruction set and according to the ranking of the plurality of initial computation units. Accordingly, the systems and methods may determine the processing program based on the one or more optimized computation units, and process the image using the processing program.

According to some embodiments of the present disclosure, a (medical) image can be processed using a processing program including one or more optimized computation units. In comparison with processing the image using GPU(s), the systems and methods disclosed in the present disclosure may process (medical) image(s) using CPU(s), and thus, the cost for purchasing and/or setting up the GPU(s) may be saved. The one or more optimized computation units may be implemented in the CPU(s), and thus, the processing efficiency of the (medical) image(s) may be guaranteed.

Figure 1:
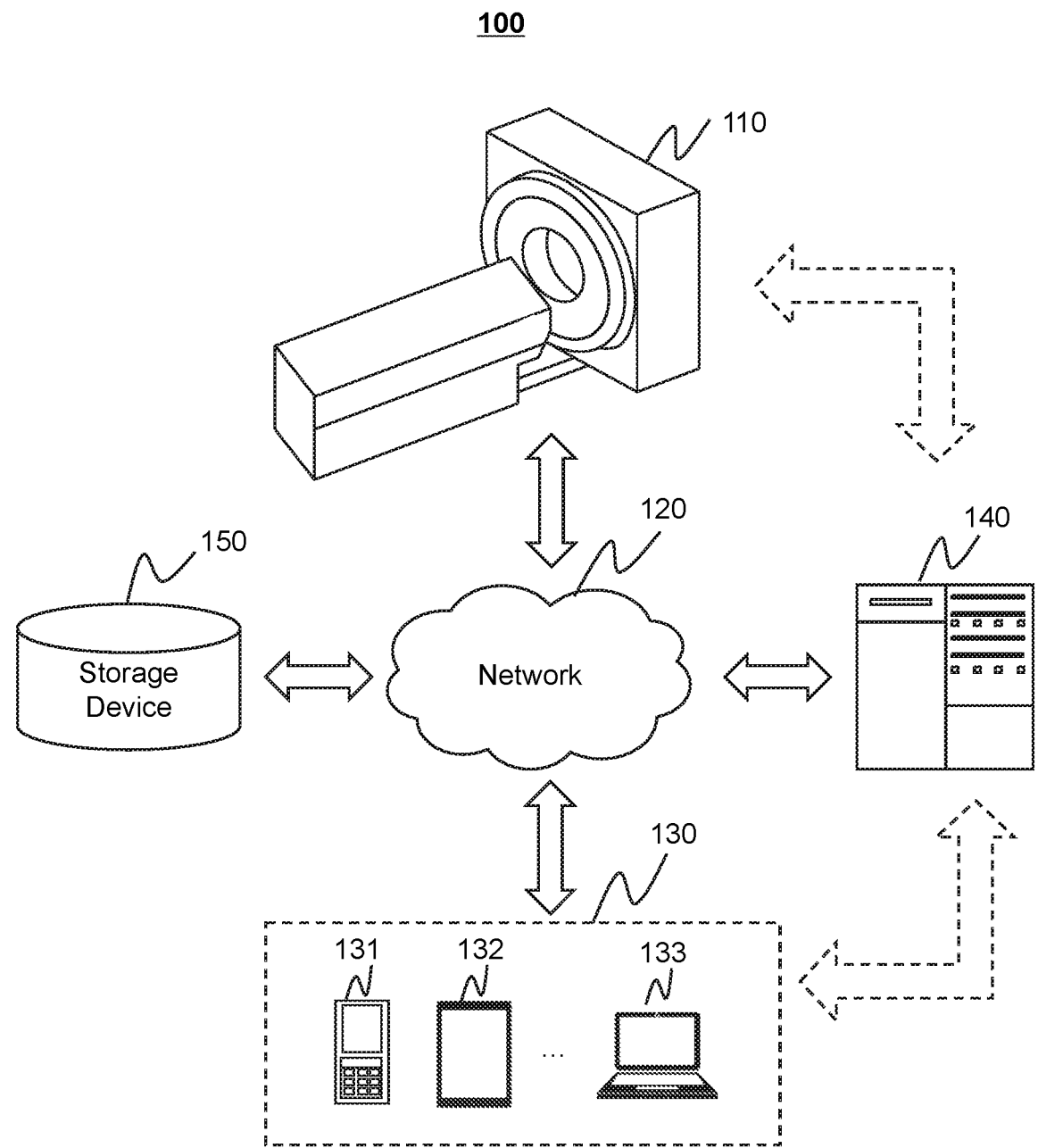
FIG. 1 is a schematic diagram illustrating an exemplary image processing system according to some embodiments of the present disclosure.

FIG. 1 is a schematic diagram illustrating an exemplary image processing system according to some embodiments of the present disclosure. The image processing system 100 may include a scanner 110, a network 120, one or more terminals 130, a processing device 140, and a storage device 150. The components in the image processing system 100 may be connected in one or more of various ways. Merely by way of example, the scanner 110 may be connected to the processing device 140 through the network 120. As another example, the scanner 110 may be connected to the processing device 140 directly as indicated by the bi-directional arrow in dotted lines linking the scanner 110 and the processing device 140. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

The scanner 110 may generate or provide image(s) via scanning a subject or a part of the subject. In some embodiments, the scanner 110 may be a medical imaging device, for example, a positron emission tomography (PET) device, a single-photon emission computed tomography (SPECT) device, a computed tomography (CT) device, a magnetic resonance imaging (MRI) device, or the like, or any combination thereof. In some embodiments, the scanner 110 may include a single-modality scanner. The single-modality scanner may include an MRI scanner, a CT scanner, a PET scanner, a cone beam CT (CBCT) imaging device, a single photon emission tomography (SPET) imaging device, an X-ray (XR) imaging device, a full-field digital mammography (FFDM) imaging device, or a digital breast tomosynthesis (DBT) imaging device, or the like, or any combination thereof. In some embodiments, the scanner 110 may include a multi-modality scanner. The multi-modality scanner may include a positron emission tomography-computed tomography (PET-CT) scanner, a positron emission tomography-magnetic resonance imaging (PET-MRI) scanner, a SPET-CT scanner, or the like, or any combination thereof. The multi-modality scanner may perform multi-modality imaging simultaneously. For example, the PET-CT scanner may generate structural X-ray CT data and functional PET data simultaneously in a single scan. The PET-MRI scanner may generate MRI data and PET data simultaneously in a single scan.

In some embodiments, the subject may include a body, substance, or the like, or any combination thereof. In some embodiments, the subject may include a specific portion of a body, such as a head, a thorax, an abdomen, or the like, or any combination thereof. In some embodiments, the subject may include a specific organ, such as a breast, an esophagus, a trachea, a bronchus, a stomach, a gallbladder, a small intestine, a colon, a bladder, a ureter, a uterus, a fallopian tube, etc. In some embodiments, the subject may include a physical model (also referred to as a mockup). The physical model may include one or more materials constructed as different shapes and/or dimensions. Different parts of the physical model may be made of different materials. Different materials may have different X-ray attenuation coefficients, different tracer isotopes, and/or different hydrogen proton contents. Therefore, different parts of the physical model may be recognized by the image processing system 100. In the present disclosure, "object" and "subject" are used interchangeably. In some embodiments, the scanner 110 may include a scanning table. The subject may be placed on the scanning table for imaging.

In some embodiments, the scanner 110 may transmit the image(s) via the network 120 to the processing device 140, the storage device 150, and/or the terminal(s) 130. For example, the image(s) may be sent to the processing device 140 for further processing or may be stored in the storage device 150.

The network 120 may include any suitable network that can facilitate the exchange of information and/or data for the image processing system 100. In some embodiments, one or more components of the image processing system 100 (e.g., the scanner 110, the terminal 130, the processing device 140, the storage device 150) may communicate information and/or data with one or more other components of the image processing system 100 via the network 120. For example, the processing device 140 may obtain one or more images from the scanner 110 via the network 120. As another example, the processing device 140 may obtain one or more images from the storage device 150 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the image processing system 100 may be connected to the network 120 to exchange data and/or information.

Figure 3:
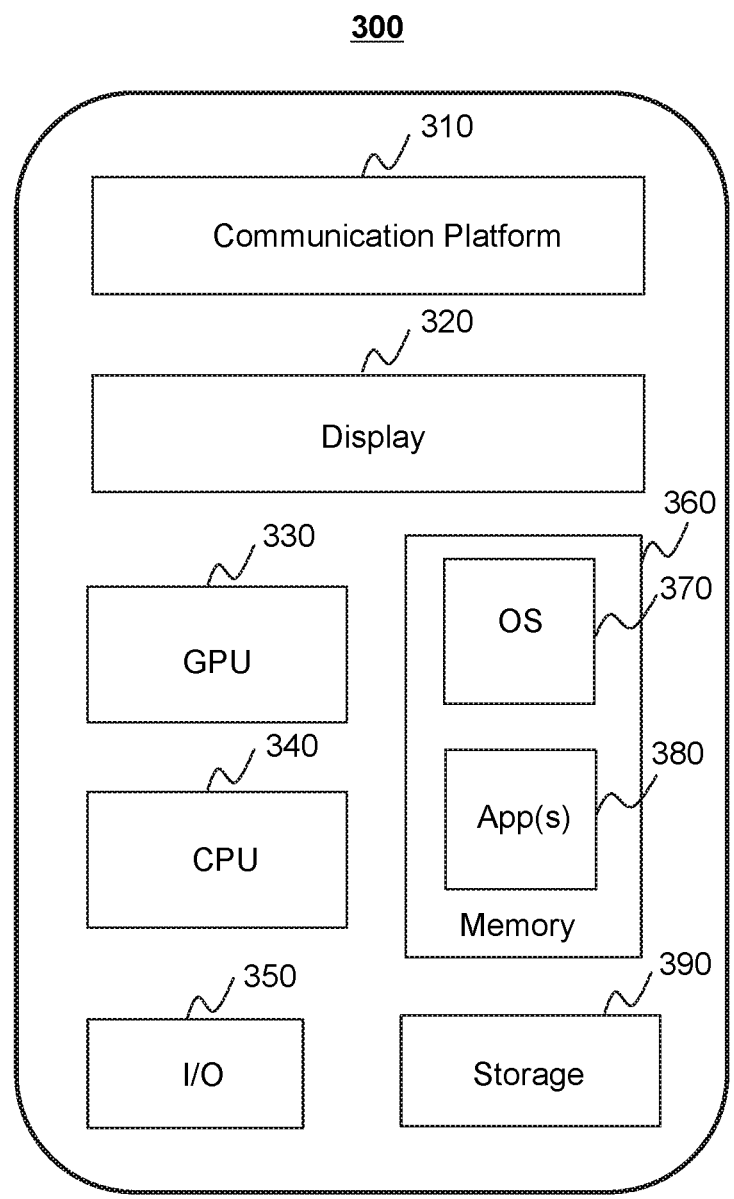
FIG. 3 is a schematic diagram illustrating exemplary hardware and/or software components of an exemplary mobile device on which the terminal may be implemented according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the scanner 110, the terminal 130, and/or the storage device 150. For example, the processing device 140 may process an image using a processing program. As another example, the processing device 140 may obtain a plurality of initial computation units of a processing program. As still another example, the processing device 140 may determine at least one instruction set that at least one processor (e.g., a CPU) supports. As still another example, the processing device 140 may determine a parameter value of at least one type of parameter for each of a plurality of initial computation units. As still another example, the processing device 140 may determine a ranking of a plurality of initial computation units based on a plurality of parameter values of a specific type of parameter for the plurality of initial computation units. As still another example, the processing device 140 may generate one or more optimized computation units by optimizing one or more initial computation units of a plurality of initial computation units using at least one instruction set and according to a ranking of the plurality of initial computation units.

In some embodiments, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage device 150 via the network 120. As another example, the processing device 140 may be directly connected to the scanner 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. In some embodiments, the processing device 140 may include a central processing unit (CPU). The CPU may include a single-core CPU, a Dual-core CPU, a Quad-core CPU, a Hex-core CPU, an Octa-core CPU, or the like, or any combination thereof.

The storage device 150 may store data, instructions, and/or any other information. In some embodiments, the storage device 150 may store data obtained from the scanner 110, the terminal 130 and/or the processing device 140. For example, the storage device 150 may store an image obtained from the scanner 110. As another example, the storage device 150 may store a processing program determined by the processing device 140. In some embodiments, the storage device 150 may store data and/or instructions that the processing device 140 may execute or use to perform exemplary methods described in the present disclosure. For example, the storage device 150 may store instructions that the processing device 140 may execute or use to determine at least one instruction set that at least one processor supports. As another example, the storage device 150 may store instructions that the processing device 140 may execute or use to determine a ranking of a plurality of initial computation units based on a plurality of parameter values of a specific type of parameter for the plurality of initial computation units. As still another example, the storage device 150 may store instructions that the processing device 140 may execute or use to generate one or more optimized computation units by optimizing one or more initial computation units of a plurality of initial computation units using at least one instruction set and according to a ranking of the plurality of initial computation units. As still another example, the storage device 150 may store instructions that the processing device 140 may execute or use to determine a processing program including one or more optimized computation units.

In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the image processing system 100 (e.g., the processing device 140, the terminal 130). One or more components of the image processing system 100 may access the data or instructions stored in the storage device 150 via the network 120. In some embodiments, the storage device 150 may be directly connected to or communicate with one or more other components of the image processing system 100 (e.g., the processing device 140, the terminal 130). In some embodiments, the storage device 150 may be part of the processing device 140.

FIG. 2 is a schematic diagram illustrating an exemplary computing device on which at least a portion of the image processing system 100 can be implemented, according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process an image obtained from the scanner 110, the storage device 150, the terminal(s) 130, and/or any other component of the image processing system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the storage device 150, the terminal(s) 130, and/or any other components of the image processing system 100. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining a processing program for processing an image.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing device 120 and the scanner 110, the storage 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the image processing system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
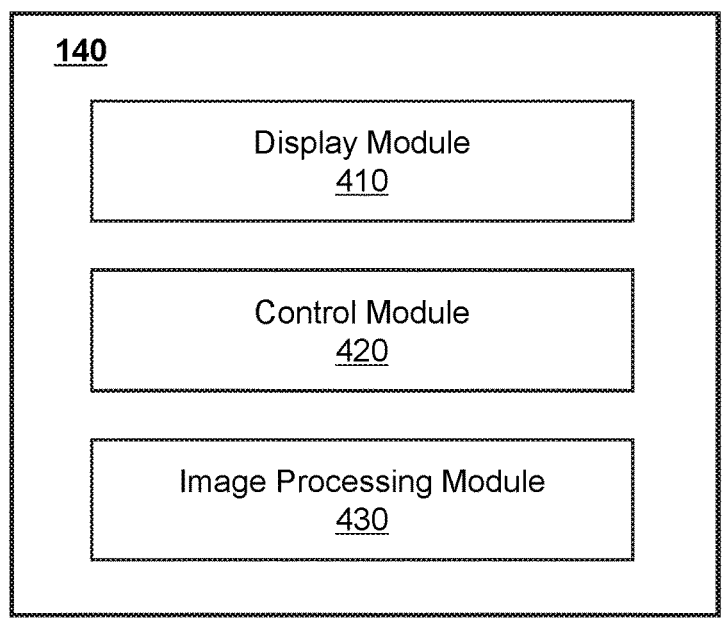
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include a display module 410, a control module 420, and an image processing module 430.

The display module 410 may be configured to display data and/or information associated with the image processing system 100. For example, the display module 410 may display one or more images generated by the scanner 110 via scanning a subject or a part of the subject. As another example, the display module 410 may display one or more processed images generated by the image processing module 430. In some embodiments, the display module 410 may include a liquid crystal display (LCD), a light-emitting diode (LED)-based display, a flat panel display, a curved screen, a television device, a cathode ray tube (CRT), a touch screen, or the like, or any combination thereof.

The control module 420 may be configured to control one or more components of the image processing system 100. For example, the control module 420 may generate instructions to adjust the position of a scanning table. As another example, the control module 420 may generate instructions to adjust the position of a tube that emits radiation beams. As still another example, the control module 420 may generate instructions to guide the scanning on a subject.

The image processing module 430 may be configured to process an image using a processing program. In some embodiments, the image processing module 430 may include a determination unit 510, an obtaining unit 520, a ranking unit 530, an optimization unit 540, and a processing unit 550 as described elsewhere in the present disclosure (e.g., FIG. 5 and descriptions thereof).

In some embodiments, before the scanning of the subject (e.g., a patient), the control module 420 may send instruction(s) to operate the scanning table to move toward a bore of the scanner 110 to adjust the position of the scanning table to a specific position preset by an operator or one or more components of the image processing system 100. After moving to the preset position, the scanning table may send a signal (indicating that the scanning table is in position) to the control module 420. The control module 420 may then send an instruction to the scanner 110 to start the scanning. The scanner 110 may receive the instruction and scan the patient. During the scanning, the scanner 110 (or the control module 420) may continuously acquire an initial image (e.g., an image reconstructed based on projection data) of the patient and transmit the initial image to the display module 410. The display module 410 may display medical image(s) associated with the initial image. In some embodiments, the image processing module 430 may perform real-time image processing on the medical image(s).

It should be noted that the above description of the processing device 140 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module facilitating data storage.

Figure 5:
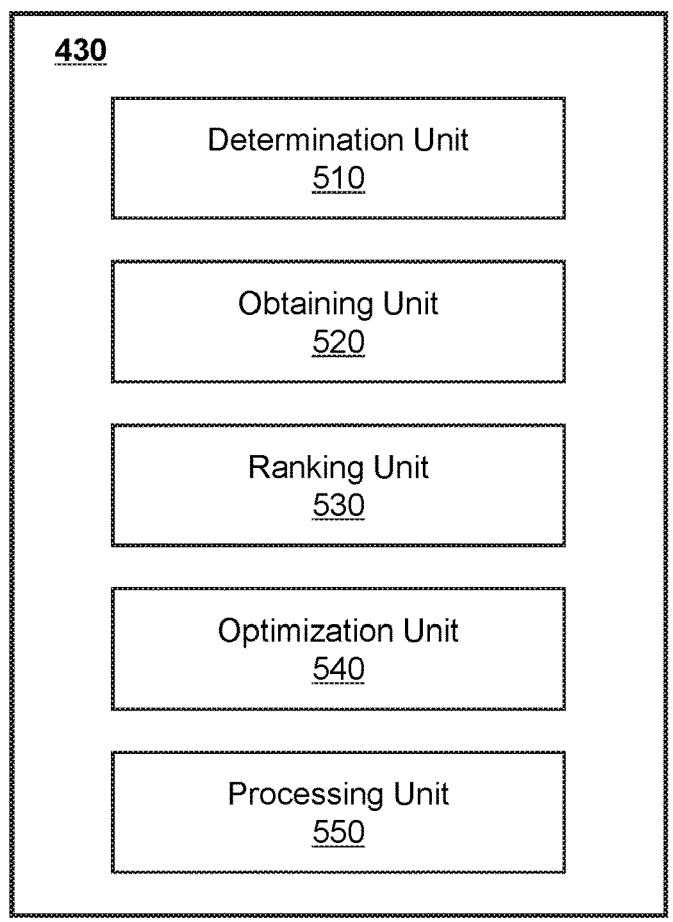
FIG. 5 is a block diagram illustrating an exemplary imaging processing module according to some embodiments of the present disclosure.

FIG. 5 is a block diagram illustrating an exemplary imaging processing module according to some embodiments of the present disclosure. The image processing module 430 may include a determination unit 510, an obtaining unit 520, a ranking unit 530, an optimization unit 540, and a processing unit 550.

The determination unit 510 may be configured to determine information associated with the image processing system 100. For example, the determination unit 510 may determine at least one instruction set that at least one processor (e.g., a CPU) supports. As another example, the determination unit 510 may determine a parameter value of at least one type of parameter for each of a plurality of initial computation units.

The obtaining unit 520 may be configured to obtain data and/or information associated with the imaging processing system 100. For example, the obtaining unit 520 may obtain one or more images. As another example, the obtaining unit 520 may obtain a plurality of initial computation units of a processing program. In some embodiments, the obtaining unit 520 may obtain the data and/or the information associated with the imaging processing system 100 from one or more components (e.g., the scanner 110, the terminal 140, and/or the storage device 150) of the image processing system 100 or an external storage device via the network 120.

The ranking unit 530 may be configured to determine a ranking of a plurality of initial computation units. For example, the ranking unit 530 may rank the plurality of initial computation units based on a plurality of parameter values of a specific type of parameter for the plurality of initial computation units. As another example, the ranking unit 530 may rank the plurality of initial computation units based on a plurality of parameter values of multiple types of parameters for the plurality of initial computation units.

The optimization unit 540 may be configured to generate one or more optimized computation units by optimizing one or more initial computation units of a plurality of initial computation units. In some embodiments, the optimization unit 540 may optimize the one or more initial computation units by using at least one instruction set and/or according to a ranking of the plurality of initial computation units. In some embodiments, the optimization unit 540 may select the one or more initial computation units to be optimized based on a plurality of parameter values of a specific type of parameter for the plurality of initial computation units and a parameter value threshold. In some embodiments, the optimization unit 540 may select the one or more initial computation units to be optimized based on the ranking of the plurality of initial computation units. For example, the optimization unit 540 may select a certain amount of initial computation units that have a relatively high ranking as the one or more initial computation units to be optimized. In some embodiments, the optimization unit 540 may determine an expected total operation time of the processing program. The optimization unit 540 may select the one or more initial computation units to be optimized from the plurality of initial computation units based on the expected total operation time and the operation time associated with each of the plurality of initial computation units, according to the ranking of the plurality of initial computation units.

The processing unit 550 may be configured to process an image using one or more processing programs. In some embodiments, the processing unit 550 may determine an (optimized) processing program based on one or more optimized computation units. The processing unit 550 may process the image using the (optimized) processing program. More descriptions for processing an image may be found elsewhere in the present disclosure (e.g., FIG. 6 and descriptions thereof).

In some embodiments, the determination unit 510 may determine whether a CPU supports one or more instruction sets. The instruction set may include an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, a virtual machine extension (VMX) instruction set, or the like, or any combination thereof. In some embodiments, the obtaining unit 520 may obtain a parameter value of at least one type of parameter for each of a plurality of initial computation units in the CPU in response to a determination that the CPU supports at least one of the one or more instruction sets. In some embodiments, the ranking unit 530 may determine a ranking of the plurality of initial computation units based on the plurality of parameter values of the at least one type of parameter for the plurality of initial computation units. In some embodiments, the optimization unit 540 may generate one or more optimized computation units by optimizing one or more initial computation units of the plurality of initial computation units using the at least one instruction set and/or according to the ranking of the plurality of initial computation units. In some embodiments, the processing unit 550 may process a medical image using the one or more optimized computation units.

It should be noted that the above description of the image processing module 430 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the image processing module 430 may further include a storage unit facilitating data storage. As another example, the obtaining unit 520 and the ranking unit 530 may be merged into a single unit.

Figure 6:
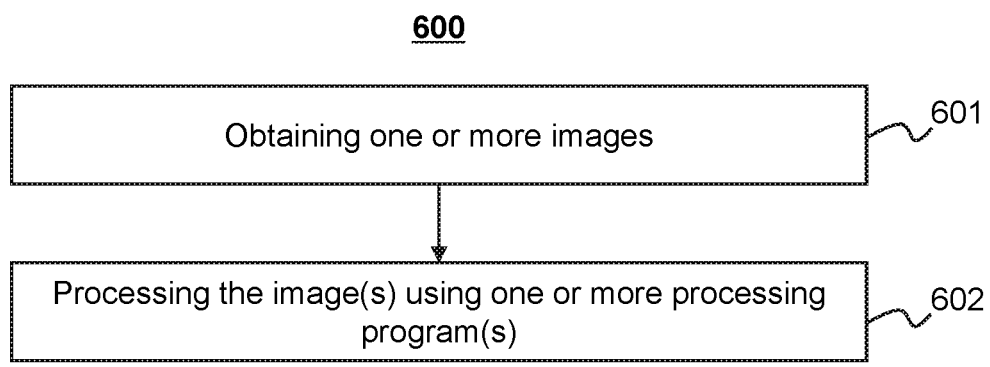
FIG. 6 is a flowchart illustrating an exemplary process for processing an image according to some embodiments of the present disclosure.

FIG. 6 is a flowchart illustrating an exemplary process for processing an image according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed.

In 601, the processing device 140 (e.g., the obtaining unit 520) may obtain one or more images. In some embodiments, the processing device 140 may obtain the image(s) from one or more components (e.g., the scanner 110, the terminal 140, and/or the storage device 150) of the image processing system 100 or an external storage device via the network 120. In some embodiments, the processing device 140 may obtain the image(s) from the I/O 230 of the computing device 200 via the communication port 240, and/or the I/O 350 of the mobile device 300 via the communication platform 310.

In some embodiments, the image(s) may include a medical image. For example, the image(s) may include a CT image, an MRI image, a PET-CT image, an SPECT-MRI image, or the like. In some embodiments, the image(s) may include a two-dimensional (2D) image, a three-dimensional (3D) image, a four-dimensional (4D) image, or the like. In some embodiments, the scanner 110 may obtain projection data via scanning a subject or a part of the subject. The processing device 140 may generate the image(s) based on projection data generated by the scanner 110.

In 602, the processing device 140 (e.g., the processing unit 550) may process the image(s) using one or more processing programs.

In some embodiments, the processing program(s) may include an image segmentation program, an image classification program, an image recognition program, an image registration program, an image fusion program, an image binarization program, or the like, or any combination thereof. For example, the image may include a region of interest (ROI), and the processing device 140 may segment or extract the ROI from the image using the image segmentation program. As another example, the processing device 140 may determine a preset group that the image belongs to using the image classification program. As a further example, the image may include an ROI (e.g., a human face), and the processing device 140 may recognize a person who owns the ROI using the image recognition program. As still a further example, the image may be a pixel image, and the processing device may convert the pixel image to a binary image using the image binarization program.

In some embodiments, the processing program may include one or more optimized computation units. As used herein, a computation unit may refer to a collection (or set) of operation instructions (or program codes). The processing device 140 may determine the one or more optimized computation units according to one or more processes as described elsewhere in the present disclosure (e.g., FIGS. 7-12, and descriptions thereof). For example, the processing device 140 may obtain a plurality of initial computation units of the processing program. The processing device 140 may determine at least one instruction set that at least one processor supports. The processing device 140 may generate the one or more optimized computation units by optimizing one or more initial computation units of the plurality of initial computation units using the at least one instruction set. In some embodiments, the processing device 140 may select a predetermined number (or count) of initial computation units to be optimized. In some embodiments, the processing device 140 may select the one or more initial computation units to be optimized based on a ranking of the plurality of initial computation units. More descriptions of the determination of the one or more optimized computations units may be found elsewhere in the present disclosure (e.g., FIGS. 7-12, and descriptions thereof).

In some embodiments, the processing program including the one or more optimized computation units may be stored in a storage device (e.g., the storage device 150) of the image processing system 100. The processing device 140 may access the storage device and retrieve the processing program before processing an image.

It should be noted that the above description of the process 600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, a storing operation may be added in process 600. The processing device 140 may store information and/or data associated with the processing program in a storage medium (e.g., the storage device 150), which is disclosed elsewhere in the present disclosure.

Figure 7:
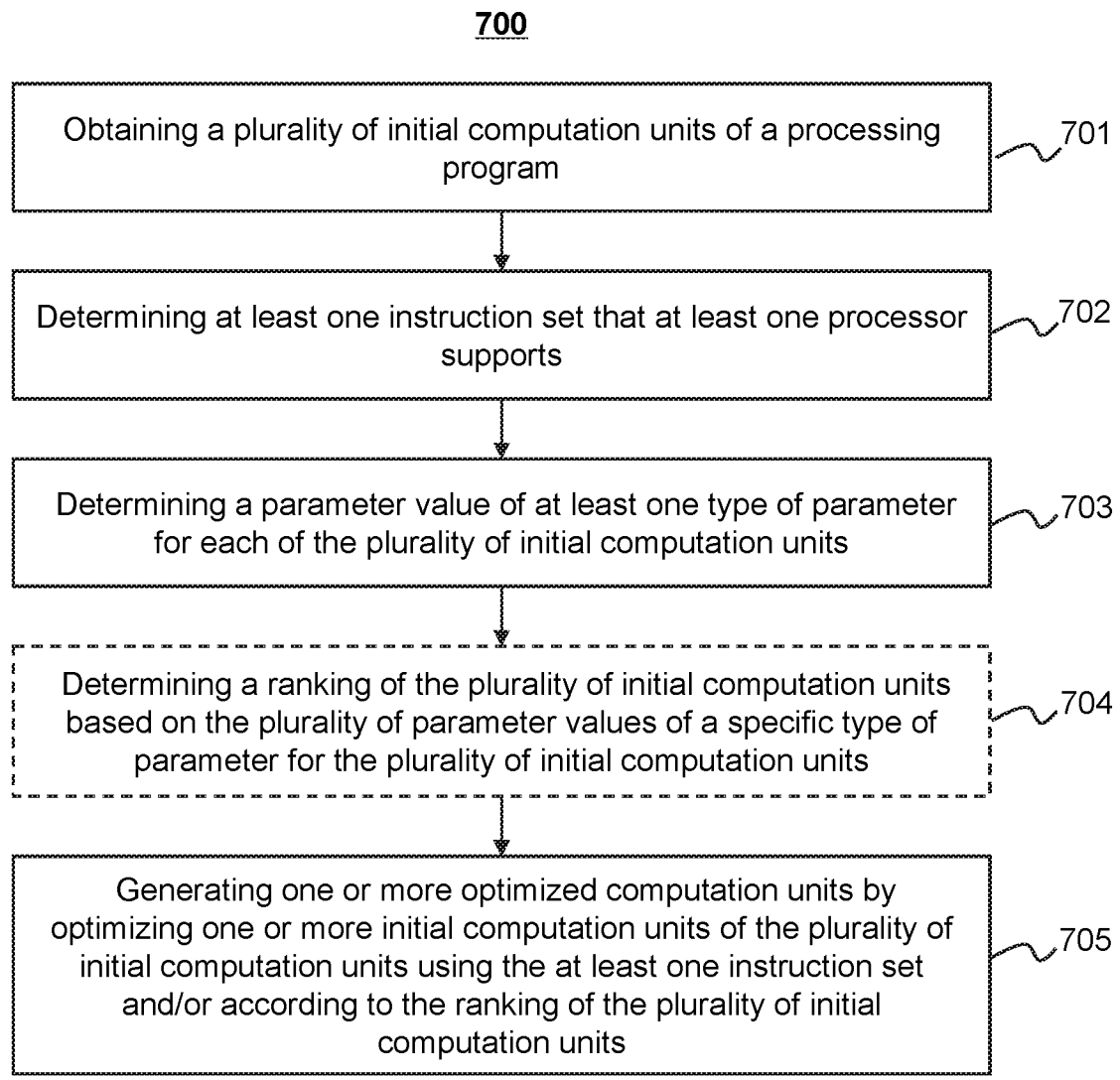
FIG. 7 is a flowchart illustrating an exemplary process for generating one or more optimized computation units according to some embodiments of the present disclosure.

FIG. 7 is a flowchart illustrating an exemplary process for generating one or more optimized computation units according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 701, the processing device 140 (e.g., the obtaining unit 520) may obtain a plurality of initial computation units of a processing program.

In some embodiments, the processing program may be used for processing an image as described elsewhere in the present disclosure (e.g., FIG. 6 and descriptions thereof). In some embodiments, the processing program may include a plurality of codes programmed by one or more developers. In some embodiments, the program codes may be executed on a CPU. As used herein, a computation unit may refer to a collection (or set) of operation instructions (or program codes). In some embodiments, the plurality of initial computation units may be generated by an operator (e.g., an engineer). In some embodiments, an initial computation unit may include codes programmed in a programming language (e.g., C, C++, C#, Java, Lisp, Smalltalk, Perl, Python, JavaScript, Ruby, etc.). In some embodiments, the plurality of initial computation units may be acquired by one or more components of the image processing system 100 according to different situations. In some embodiments, the plurality of initial computation units may be stored in a storage device (e.g., the storage device 150) of the image processing system 100. The processing device 140 may access the storage device and retrieve the plurality of initial computation units. In some embodiments, if the operation instructions (or program codes) of the initial computation unit(s) are executed in a CPU, a plurality of arithmetic and/or bitwise operations on binary numbers may be performed by an arithmetic logic unit (ALU) of the CPU. However, in some embodiments, because of the programming language and/or instructions used in the program codes, the operations performed by the ALU may not fully utilize CPU resources, and accordingly, the operation efficiency of the processing program may be affected. Therefore, it is desirable to optimize the processing program such that the CPU resource utilization efficiency may be improved when executing the optimized processing program and the time for processing the image(s) may be shortened.

In 702, the processing device 140 (e.g., the determination unit 510) may determine at least one instruction set that at least one processor supports.

In some embodiments, the at least one processor may include a central processing unit (CPU). As used herein, a CPU may refer to an electronic circuitry within a computer (or computing device) that may execute instructions of a computer program by performing one or more basic arithmetic, logical, control and input/output (I/O) operations specified by the instructions. The CPU may function as a computing core and a control core of a computer. In some embodiments, the CPU may include an arithmetic unit, a cache memory, and a bus configured to realize the data transmission and state control between them.

As used herein, an instruction set may refer to a group of commands programmed in machine language that can be recognized and performed by a CPU. The instruction set may perform mathematical operations such as addition, subtraction, multiplication, and division on one or more initial computation units in the CPU to realize the optimization of the initial computation unit(s). In some embodiments, the instruction set may include an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, a virtual machine extension (VMX) instruction set, or the like, or any combination thereof.

In some embodiments, the processing device 140 may determine a plurality of first instruction sets based on the initial computation unit(s) of the processing program. In some embodiments, the first instruction set(s) may be selected from a pool of instruction sets (e.g., manually) by an operator (e.g., an engineer). The pool of instruction sets may include various instruction sets supported by various CPUs (e.g., instruction sets x86, extended memory 64 technology (EM64T), MMX, SSE, SSE2, SSE3, SSSE3 (super SSE3), SSE4A, SSE4.2, AVX, AVX2, AVX-512, and virtual machine extension (VMX) supported by Intel CPU, instruction sets x86, x86-64, and 3D-Now supported by AMD CPU, etc.). In some embodiments, the first instruction set(s) may be determined or selected by one or more components of the image processing system 100 according to application scenario(s). For example, the processing device 140 may determine the first instruction set(s) based on operation characteristics of the initial computation unit(s). In some embodiments, the processing device 140 may determine the first instruction set(s) according to optimization purpose(s). For example, the processing device 140 may select the first instruction set(s) that can optimize operation times of the initial computation unit(s). As another example, the processing device may select the first instruction set(s) that may optimize operational power consumptions of the initial computation unit(s).

In some embodiments, the processing device 140 may further determine one or more second instruction sets that the at least one processor supports from the plurality of first instruction sets. In some embodiments, the processing device 140 may determine the second instruction set(s) that the at least one processor supports based on CPU model and/or parameters (e.g., basic frequency, external clock, multiple frequency, etc.) of the at least one processor (e.g., the CPU). In some embodiments, the processing device 140 may send a test instruction to the at least one processor, and determine the second instruction set(s) that the at least one processor supports based on a corresponding return value. In some embodiments, one or more instruction sets may be preset in one or more components of the image processing system 100. The processing device 140 may automatically determine whether the CPU supports the one or more instruction sets when it starts up.

In some embodiments, the processing device 140 may select a target instruction set from the one or more second instruction sets that the at least one processor supports for optimizing one or more initial computation units. In some embodiments, the processing device 140 may select the target instruction set based on performances of the one or more second instruction sets that the at least one processor supports according to specific optimization purpose(s). For example, the processing device 140 may select an instruction set with highest computational capability from the one or more second instruction sets as the target instruction set.

In 703, the processing device 140 (e.g., the determination unit 510) may determine a parameter value of at least one type of parameter for each of the plurality of initial computation units.

In some embodiments, each of the plurality of initial computation units may have one or more types of parameters. As used herein, a type of parameter for an initial computation unit may indicate an operational performance of the initial computation unit. In some embodiments, the type of parameter for the initial computation unit may include an operation time of the initial computation unit, a resource capacity of the at least one processor occupied by the initial computation unit, a count of instructions included in the initial computation unit, or the like, or any combination thereof. As used herein, "an operation time of an initial computation unit" may refer to a total time it takes to execute all instructions in the initial computation unit. As used herein, "a resource of the at least one processor occupied by an initial computation unit" may refer to a resource capacity of a register and/or a cache of the at least one processor occupied by the initial computation unit.

In some embodiments, each of the one or more types of parameters for each of the plurality of initial computation units may have a parameter value. In some embodiments, the processing device 140 may determine the parameter value of each type of parameter for each of the plurality of initial computation units by executing all instructions in the initial computation unit for a plurality of times. For example, the processing device 140 may determine a parameter value of an operation time for an initial computation unit by executing all instructions in the initial computation unit for a plurality of times. Specifically, the processing device 140 may determine a plurality of candidate parameter values of the operation time for the initial computation unit by executing all instructions in the initial computation unit for the plurality of times. The processing device 140 may also determine an average value of the plurality of candidate parameter values by dividing a sum of the plurality of candidate parameter values by the number (or count) of execution times. The processing device 140 may further determine the average value as the parameter value of the operation time for the initial computation unit. Merely for illustration purpose, if the processing device 140 executes all instructions in an initial computation unit A for three times, and the candidate parameter values of the operation time for the initial computation unit A are t1, t2, and t3, respectively. In this situation, the processing device 140 may determine that the parameter value of the operation time for the initial computation unit A is (t1+t2+t3)/3.

In some embodiments, one or more parameter values corresponding to one or more types of parameters for each of the plurality of initial computation units may be stored in a storage device (e.g., the storage device 150) of the image processing system 100 or an external storage device. The processing device 140 may access the storage device and retrieve the one or more parameter values corresponding to one or more types of parameters for each of the plurality of initial computation units.

In 704, the processing device 140 (e.g., the ranking unit 530) may determine a ranking of the plurality of initial computation units based on the plurality of parameter values of a specific type of parameter for the plurality of initial computation units. In some embodiments, the specific type of parameter may be determined by an engineer. In some embodiments, the specific type of parameter may be determined by the processing device 140 according to an optimization purpose. For example, if the optimization purpose is to improve operational efficiency, the processing device 140 may determine a type of parameter associated with operational efficiency as the specific type of parameter. As another example, if the optimization purpose is to save electricity, the processing device 140 may determine a type of parameter associated with electricity consumption as the specific type of parameter. In some embodiments, the ranking of the plurality of initial computation units may indicate (or be associated with) an optimization priority of the plurality of initial computation units.

In some embodiments, the processing device 140 may rank the plurality of initial computation units based on the plurality of parameter values of the specific type of parameter for the plurality of initial computation units. In some embodiments, an initial computation unit having a parameter value that may lead to a relatively slow operating speed of the at least one processor may have a relatively high ranking. For example, an initial computation unit with a relatively long operation time may lead to a relatively slow operating speed of the at least one processor. Accordingly, the processing device 140 may rank the plurality of initial computation units according to their operation times in a descending order. Merely for illustration purpose, if a processing program includes an initial computation unit A having an operation time of 10 ms, an initial computation unit B having an operation time of 20 ms, and an initial computation unit C having an operation time of 30 ms, then the processing device 140 may determine a ranking of the initial computation units as: initial computation unit C, initial computation unit B, initial computation unit A. As another example, an initial computation unit that occupies more resource capacity of the at least one processor may lead to a relatively slow operating speed of the at least one processor. Accordingly, the processing device 140 may rank the plurality of initial computation units according to the resource capacity of the at least one processor occupied by each of the plurality of initial computation units in a descending order. As still another example, an initial computation unit with a relatively large number (or count) of instructions may have more abundant arithmetic logic, which may lead to a relatively slow operating speed of the at least one processor. Accordingly, the processing device 140 may rank the plurality of initial computation units according to the count of instructions included in each of the plurality of initial computation units in a descending order.

In some embodiments, the processing device 140 may rank the plurality of initial computation units based on a plurality of parameter values of multiple types of parameters for the plurality of initial computation units. For example, for each of the plurality of initial computation units, the processing device 140 may determine a score for each type of the multiple types of parameters associated with the each of the plurality of initial computation units. The processing device 140 may determine a total score for the each of the plurality of initial computation units based on the score for the each type of the multiple types of parameters associated with the each of the plurality of initial computation units. The processing device 140 may determine the ranking of the plurality of initial computation units based on the total scores of the plurality of initial computation units. More descriptions of the determination of the ranking of the plurality of initial computation units may be found elsewhere in the present disclosure (e.g., FIG. 10 and descriptions thereof).

In 705, the processing device 140 (e.g., the optimization unit 540) may generate one or more optimized computation units by optimizing one or more initial computation units of the plurality of initial computation units using the at least one instruction set and/or according to the ranking of the plurality of initial computation units.

In some embodiments, the processing device 140 may select the one or more initial computation units to be optimized based on the plurality of parameter values of the specific type of parameter for the plurality of initial computation units and a parameter value threshold. For example, the processing device 140 may select the one or more initial computation units based on an operation time associated with each of the plurality of initial computation units and an operation time threshold. Specifically, the processing device 140 may determine whether the operation time associated with each of the plurality of initial computation units is larger than the operation time threshold. In response to a determination that an operation time associated with an initial computation unit is larger than the operation time threshold, the processing device 140 may determine the initial computation unit as one of the one or more initial computation units to be optimized.

In some embodiments, the processing device 140 may select the one or more initial computation units to be optimized based on the ranking of the plurality of initial computation units. In some embodiments, the processing device 140 may select a certain amount of initial computation units that have a relatively high ranking as the one or more initial computation units to be optimized. For example, the processing device 140 may select the one or more initial computation units (e.g., top 1, top 2, top 5, top 10, top 1%, top 5%, top 10%, top 30%) from the plurality of initial computation units based on the ranking result.

In some embodiments, the processing device 140 may determine an expected total operation time of the processing program. The processing device 140 may select the one or more initial computation units to be optimized from the plurality of initial computation units based on the expected total operation time and the operation time associated with each of the plurality of initial computation units, according to the ranking of the plurality of initial computation units. For example, the processing device 140 may select the one or more initial computation units based on an expected minimum operation time associated with each of the plurality of initial computation units, and the expected total operation time, according to the ranking of the plurality of initial computation units. The processing device 140 may optimize the one or more initial computation units using the at least one instruction set. For example, the processing device 140 may optimize the one or more initial computation units using the target instruction set as described in connection with operation 702. In some embodiments, if an initial computation unit that has a relatively large operation time is optimized, the total operation time of the processing program may be shortened more effectively. Therefore, the initial computation unit that has a relatively large operation time may have a relatively high priority for optimization. More descriptions of the generation of the one or more optimized computation units may be found elsewhere in the present disclosure (e.g., FIG. 8 and descriptions thereof).

In some embodiments, the processing device 140 may determine an expected total operation time of the processing program. In some embodiments the processing device 140 may optimize one or more of the plurality of initial computation units in sequence based on the ranking of the plurality of initial computation units. After optimizing an initial computation unit, the processing device 140 may determine an estimated total operation time of the processing program based on the operation times associated with the one or more optimized computation units and the rest of the plurality of initial computation units. The processing device 140 may determine whether the estimated total operation time is less than or equal to the expected total operation time. In response to a determination that the estimated total operation time is less than or equal to the expected total operation time, the processing device 140 may terminate the optimization of the plurality of initial computation units. In response to a determination that the estimated total operation time is larger than the expected total operation time, the processing device 140 may determine whether the optimizing operation has been performed on all of the plurality of initial computation units. In response to a determination that the optimizing operation has not been performed on all of the plurality of initial computation units, the processing device 140 may further optimize another initial computation unit in the rest of the plurality of initial computation units according to the ranking of the rest of the plurality of initial computation units. For example, the processing device 140 may optimize an initial computation unit with a highest ranking in the rest of the plurality of initial computation units. In response to a determination that the optimizing operation has been performed on all of the plurality of initial computation units, the processing device 140 may generate, in the processing program, an instruction for adding one or more threads or invoking multi threads for processing the image in the at least one processor. More descriptions of the generation of the one or more optimized computation units may be found elsewhere in the present disclosure (e.g., FIG. 9 and descriptions thereof).

It should be noted that the above description of the process 700 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, operation 701 and operation 702 may be merged into a single operation. As another example, a storing operation may be added in process 700. The processing device 140 may store information and/or data associated with the plurality of initial computation units in a storage medium (e.g., the storage device 150), which is disclosed elsewhere in the present disclosure. As a further example, operation 704 may be omitted, and the processing device 140 may determine the one or more initial computation units to be optimized randomly, or based on an instruction of an engineer, or based on the parameter values of one or more specific types of parameter for the plurality of initial computation units.

Figure 8:
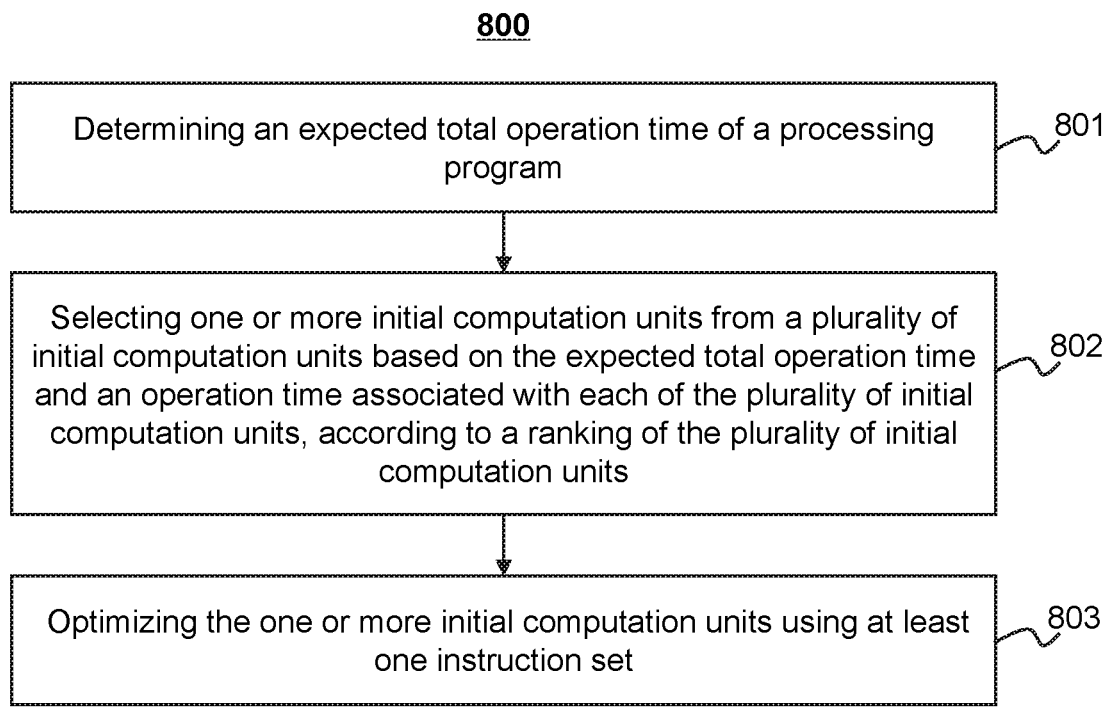
FIG. 8 is a flowchart illustrating an exemplary process for generating one or more optimized computation units according to some embodiments of the present disclosure.

FIG. 8 is a flowchart illustrating an exemplary process for generating one or more optimized computation units according to some embodiments of the present disclosure. In some embodiments, at least part of process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, operation 705 illustrated in FIG. 7 may be performed according to the process 800.

In 801, the processing device 140 (e.g., the optimization unit 540) may determine an expected total operation time of a processing program.

As used herein, the expected total operation time of the processing program may refer to a sum of a plurality of parameter values of operation times for the plurality of initial computation units in the processing program under an ideal situation. The expected total operation time of the processing program may be regarded as an optimization purpose. The expected total operation time may be determined (e.g., manually) by an operator (e.g., an engineer), or be determined by one or more components of the image processing system 100 according to different situations. In some embodiments, the expected total operation time may be determined based on user experience and/or CPU model of the at least one processor (e.g., a CPU). Merely by way of example, the expected total operation time determined may be less than 200 milliseconds.

In 802, the processing device 140 (e.g., the optimization unit 540) may select one or more initial computation units from a plurality of initial computation units based on the expected total operation time, and/or an operation time associated with each of the plurality of initial computation units, according to a ranking of the plurality of initial computation units.

In some embodiments, the processing device 140 may select the one or more initial computation units based on an expected minimum operation time associated with each of the plurality of initial computation units, and the expected total operation time, according to the ranking of the plurality of initial computation units. As used herein, "an expected minimum operation time associated with an initial computation unit" may refer to a minimum operation time for the initial computation unit after optimization. In some embodiments, the expected minimum operation time of the initial computation unit may be determined based on the performance of an instruction set used to optimize the initial computation unit and performance of the at least one processor (e.g., the CPU). Merely by way of example, if an operation time for an initial computation unit A is 100 ms, the at least one processor includes four threads, and the AVX instruction set processes eight digits in a single step. Accordingly, the expected minimum operation time for the initial computation unit A after optimization (i.e., the optimized computation unit A) may be 3.125 ms (i.e., 100 ms/(8×4)=3.125 ms). In some embodiments, the expected total operation time may be no less than a sum of the expected minimum operation times associated with the plurality of initial computation units. In some embodiments, if the sum of the expected minimum operation times associated with the plurality of initial computation units is less than the expected total operation time, only a portion of the plurality of initial computation units may need to be optimized to achieve the optimization purpose.

Merely for illustration purpose, if a processing program includes an initial computation unit A having an operation time of 10 ms, an initial computation unit B having an operation time of 20 ms, an initial computation unit C having an operation time of 30 ms, then the processing device 140 may determine a ranking of the initial computation units as: initial computation unit C, initial computation unit B, initial computation unit A. If the minimum operation times for the initial computation unit A, the initial computation unit B, and the initial computation unit C are determined as: 5 ms, 10 ms, and 15 ms, respectively, and the expected total operation time is 35 ms, then the processing device 140 may select the initial computation unit C and the initial computation unit B for optimization. That is, the processing device 140 may first optimize the initial computation unit C, and then optimize the initial computation unit B. Accordingly, an estimated total operation time of the processing program (i.e., 15 ms+10 ms+10 ms=35 ms) after optimization may be no larger than the expected total operation time of the processing program, which means the optimization purpose can be achieved without optimizing the initial computation unit A. Therefore, the processing device 140 may select the initial computation unit C and the initial computation unit B for optimization to achieve the optimization purpose.

In 803, the processing device 140 (e.g., the optimization unit 540) may optimize the one or more initial computation units using at least one instruction set.

In some embodiments, the processing device 140 may optimize the one or more initial computation units one by one using the at least one instruction set. In some embodiments, the processing device 140 may optimize the one or more initial computation units simultaneously using the at least one instruction set.

In some embodiments, the processing device 140 may optimize the one or more initial computation units by compiling instructions included in the one or more initial computation units using (or based on) the at least one instruction set. The processing device 140 may further obtain an optimized processing program based on the one or more optimized computation units and the rest of the plurality of computation units that are not optimized (if any). In some embodiments, the optimized processing program may be presented as an executable file. For example, the processing device 140 may generate an executable file based on the one or more optimized computation units and the rest of the plurality of computation units that are not optimized (if any).

In some embodiments, the optimized processing program including the one or more optimized computation units may be stored in a storage device (e.g., the storage device 150) of the image processing system 100. The processing device 140 may access the storage device and retrieve the optimized processing program before processing an image.

It should be noted that the above description of the process 600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, an operation for determining an expected minimum operation time for each of the plurality of initial computation units may be added before operation 802.

Figure 9:
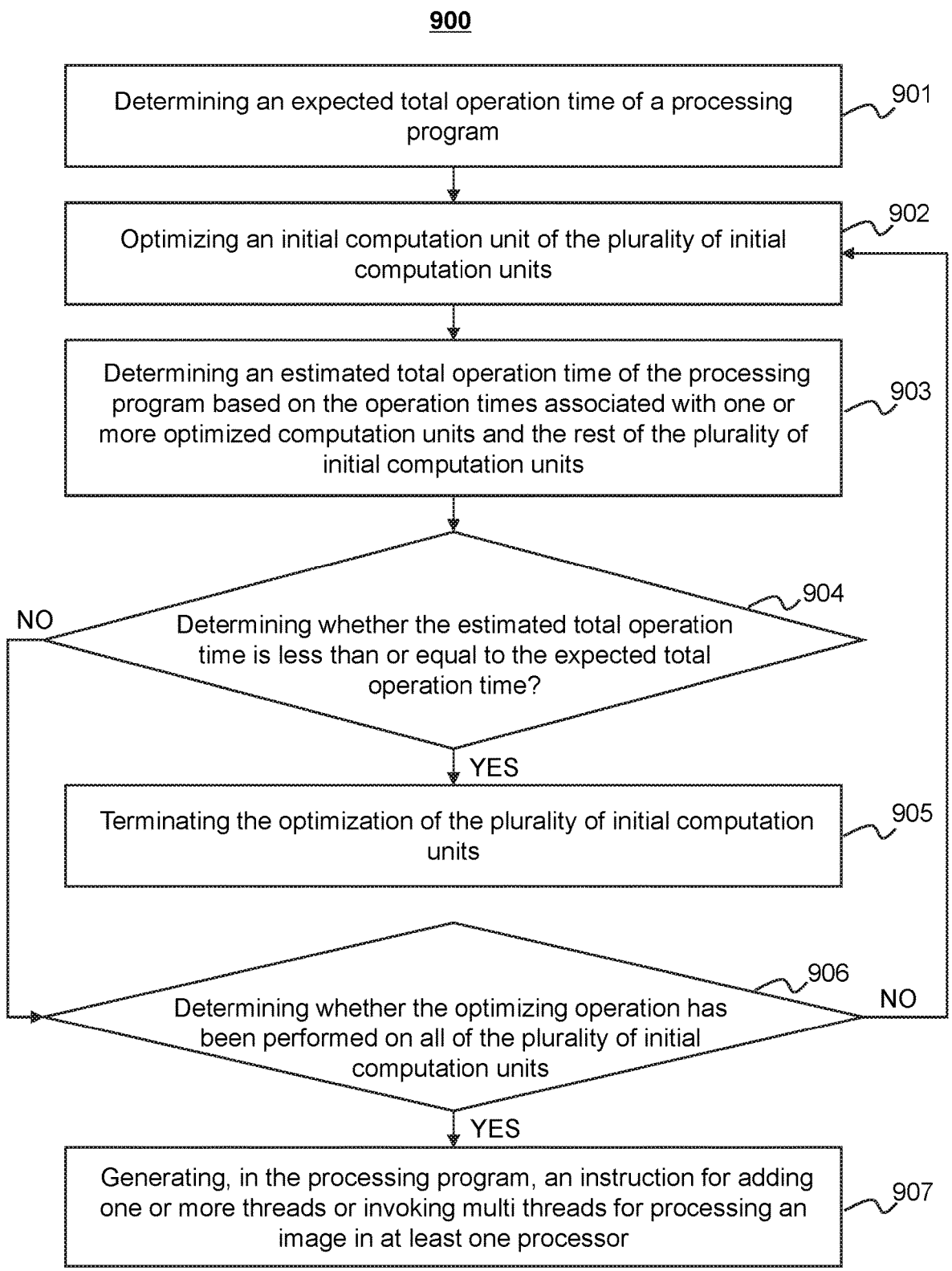
FIG. 9 is a flowchart illustrating an exemplary process for generating one or more optimized computation units according to some embodiments of the present disclosure.

FIG. 9 is a flowchart illustrating an exemplary process for generating one or more optimized computation units according to some embodiments of the present disclosure. In some embodiments, at least part of process 900 may be performed by the processing device 140 (implemented in, for example, the computing device 200 shown in FIG. 2). For example, the process 900 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting. In some embodiments, operation 705 illustrated in FIG. 7 may be performed according to the process 900.

In 901, the processing device 140 (e.g., the optimization unit 540) may determine an expected total operation time of a processing program. More descriptions of the determination of the expected total operation time of the processing program may be found elsewhere in the present disclosure (e.g., operation 801 in FIG. 8 and descriptions thereof).

In 902, the processing device 140 (e.g., the optimization unit 540) may optimize an initial computation unit of the plurality of initial computation units. In some embodiments, the processing device 140 may optimize one or more of the plurality of initial computation units in sequence based on the ranking of the plurality of initial computation units. For example, the processing device 140 may optimize an initial computation unit with a highest ranking in the plurality of initial computation units.

In 903, the processing device 140 (e.g., the optimization unit 540) may determine an estimated total operation time of the processing program based on the operation times associated with one or more optimized computation units and the rest of the plurality of initial computation units that are not optimized.

In some embodiments, after optimizing an initial computation unit, the processing device 140 may determine an estimated total operation time of the processing program. In some embodiments, the processing device 140 may determine the estimated total operation time of the processing program based on a sum of the operation times associated with the one or more optimized computation units and the rest of the plurality of initial computation units that are not optimized.

In 904, the processing device 140 (e.g., the optimization unit 540) may determine whether the estimated total operation time is less than or equal to the expected total operation time.

In response to a determination that the estimated total operation time is less than or equal to the expected total operation time, process 900 may proceed to operation 905. In 905, the processing device 140 (e.g., the optimization unit 540) may terminate the optimization process. The processing device 140 may determine an optimized processing program based on the one or more optimized computation units and the rest of the plurality of initial computation units that are not optimized.

In response to a determination that the estimated total operation time is greater than the expected total operation time, process 900 may proceed to operation 906. In 906, the processing device 140 (e.g., the optimization unit 540) may determine whether the optimizing operation has been performed on all of the plurality of initial computation units.

In response to a determination that the optimizing operation has not been performed on all of the plurality of initial computation units, the processing device 140 may execute process 900 to return to operation 902 to further optimize another initial computation unit of the rest of plurality of initial computation units according to the ranking of the rest of the plurality of initial computation units. For example, the processing device 140 may optimize an initial computation unit with a highest ranking in the rest of the plurality of initial computation units. In some embodiments, operations 902 through 906 may be iteratively performed until the estimated total operation time is less than or equal to the expected total operation time or the optimizing operation has been performed on all of the plurality of initial computation units. If the estimated total operation time is less than or equal to the expected total operation time, process 900 may proceed to 905 to terminate the optimization process. If the optimizing operation has been performed on all of the plurality of initial computation units, process 900 may proceed to 907.

Merely by way of example, if a processing program includes an initial computation unit A having an operation time of 10 ms, an initial computation unit B having an operation time of 20 ms, an initial computation unit C having an operation time of 30 ms, the expected total operation time is 35 ms, and the ranking of the initial computation units is determined as: initial computation unit C, initial computation unit B, initial computation unit A, then the processing device 140 may optimize the initial computation unit C first. If the operation time of the optimized computation unit C is 15 ms after the first optimization, then the estimated total operation time of the processing program may be 45 ms (i.e., 10 ms+20 ms+15 ms=45 ms). The estimated total operation time of the processing program after the first optimization is larger than the expected total operation time, and then the processing device 140 may optimize the initial computation unit B. If the operation time of the optimized computation unit B is 10 ms after the second optimization, then the estimated total operation time of the processing program may be 35 ms (i.e., 10 ms+10 ms+15 ms=35 ms). The estimated total operation time of the processing program after the second optimization is no larger than the expected total operation time, and then the optimization process may be terminated. An optimized processing program may be determined based on the initial computation unit A, the optimized computation unit B, and the optimized computation unit C.

In 907, the processing device 140 (e.g., the optimization unit 540) may generate, in the processing program, an instruction for adding one or more threads or invoking multi threads for processing an image in at least one processor. That is, if all of the plurality of initial computation units of the processing program are optimized, and the expected total operation time (or the optimization purpose) is still not achieved, the processing device 140 may improve the operation efficiency of the processing program using multithreading.

As used herein, a thread may refer to a sequence of programmed instructions that can be managed independently by a scheduler of an operating system installed on a processor. Multithreading may refer to the ability of a processor (e.g., the CPU) to execute multiple processes or threads concurrently. For example, when a process of processing an image is started, memory and resources of the at least one processor may be allocated to run the process. Each thread in the process may share the memory and resources. In a single-threaded process, the image may be processed on a single thread. In a multithreaded process, the image may be processed on two or more threads at the same time. Accordingly, the speed of image processing may be improved.

It should be noted that the above description of the process 900 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure.

Figure 10:
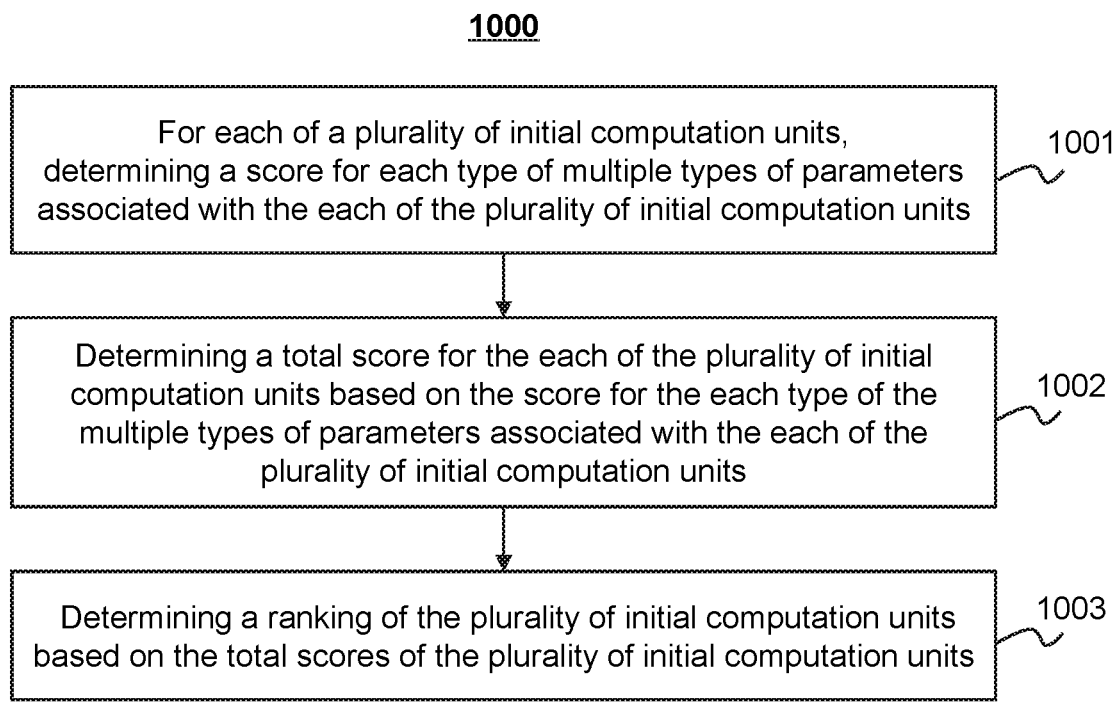
FIG. 10 is a flowchart illustrating an exemplary process for determining a ranking of a plurality of initial computation units according to some embodiments of the present disclosure.

FIG. 10 is a flowchart illustrating an exemplary process for determining a ranking of a plurality of initial computation units according to some embodiments of the present disclosure. In some embodiments, at least part of process 1000 may be performed by the processing device 140 (implemented in, for example, the computing device 200 shown in FIG. 2). For example, the process 1000 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting. In some embodiments, each of the plurality of initial computation units may have multiple types of parameters, and operation 704 illustrated in FIG. 7 may be performed according to the process 1000.

In 1001, for each of a plurality of initial computation units, the processing device 140 (e.g., the ranking unit 530) may determine a score for each type of multiple types of parameters associated with the each of the plurality of initial computation units.

In some embodiments, for the each type of the multiple types of parameters, the processing device 140 may determine the score for the each type associated with the each of the plurality of initial computation units by normalizing the plurality of parameter values of the each type associated with the plurality of initial computation units. In some embodiments, the multiple types of parameters may include an operation time of the each of the plurality of initial computation units, a resource capacity of the at least one processor occupied by the each of the plurality of initial computation units, and a count of instructions included in the each of the plurality of initial computation units, as described elsewhere in the present disclosure (e.g., FIG. 7 and descriptions thereof).

Merely for illustration purposes, if a processing program includes an initial computation unit A, an initial computation unit B, an initial computation unit C, and the parameter values of the operation time for the initial computation unit A, the initial computation unit B, and the initial computation unit C are a, b, and c, respectively, then the processing device 140 may determine that the score for the operation time associated with the initial computation unit A is Pa (i.e., Pa=a/(a+b+c)), the score for the operation time associated with the initial computation unit B is Pb (i.e., Pb=b/(a+b+c)), the score for the operation time associated with the initial computation unit C is Pc (i.e., Pc=c/(a+b+c)), wherein Pa+Pb+Pc=1. Similarly, the processing device 140 may determine the scores for the resource capacities of the at least one processor occupied by the initial computation unit A, the initial computation unit B, and the initial computation unit C, based on parameter values of the resource capacities of the at least one processor occupied by the initial computation unit A, the initial computation unit B, and the initial computation unit C. Merely for illustration purpose, the processing device 140 may determine that the scores for the resource capacities of the at least one processor occupied by the initial computation unit A, the initial computation unit B, and the initial computation unit C are Qa, Qb, and Qc, respectively. Similarly, the processing device 140 may determine the scores for the counts of instructions included in the initial computation unit A, the initial computation unit B, and the initial computation unit C, based on parameter values of counts of instructions included in the initial computation unit A, the initial computation unit B, and the initial computation unit C. Merely for illustration purpose, the processing device 140 may determine that the scores for the counts of instructions included in the initial computation unit A, the initial computation unit B, and the initial computation unit C are Ra, Rb, and Rc, respectively.

In 1002, the processing device 140 (e.g., the ranking unit 530) may determine a total score for the each of the plurality of initial computation units based on the score for the each type of the multiple types of parameters associated with the each of the plurality of initial computation units.

In some embodiments, the processing device 140 may determine the total score for the each of the plurality of initial computation units based on a weighted mean of the scores for the multiple types of parameters associated with the each of the plurality of initial computation units. For example, the processing device 140 may determine a total score for an initial computation unit based on the score for each type of the multiple types of parameters associated with the initial computation unit and a weight corresponding to the each type of the multiple types of parameters. As used herein, a weight corresponding to a type of parameter associated with an initial computation unit may indicate the importance of the type of parameter in the optimization process.

Merely for illustration purpose, if the score for the operation time associated with the initial computation unit A is Pa, the score for the resource capacity of the at least one processor occupied by the initial computation unit A is Qa, the score for the count of instructions included in the initial computation unit A is Ra, the weight corresponding to the operation time is W1, the weight corresponding to the resource capacity of the at least one processor occupied by the initial computation unit A is W2, and the weight corresponding to the count of instructions included in the initial computation unit A is W3, then the processing device 140 may determine that the total score for the initial computation unit A is PA=(Pa×W1+Qa×W2+Ra×W3)/(W1+W2+W3). Similarly, the processing device 140 may determine the total score for the initial computation unit B (e.g., PB=(Pb×W1+Qb×W2+Rb×W3)/(W1+W2+W3)), and the total score for the initial computation unit C (e.g., PC=(Pc×W1+Qc×W2+Rc×W3)/(W1+W2+W3)).

In 1003, the processing device 140 (e.g., the ranking unit 530) may determine a ranking of the plurality of initial computation units based on the total scores of the plurality of initial computation units.

In some embodiments, the processing device 140 may rank the plurality of initial computation unites according to their total scores in a descending order. Merely for illustration purpose, if PA>PB>PC, the processing device 140 may determine the ranking of the initial computation units as: initial computation unit A, initial computation unit B, initial computation unit C. Accordingly, the processing device 140 may first optimize the initial computation unit A. In some embodiments, the processing device 140 may then optimize the initial computation unit B. In some embodiments, the processing device 140 may further optimize the initial computation unit C.

It should be noted that the above description of the process 1000 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure.

Figure 11:
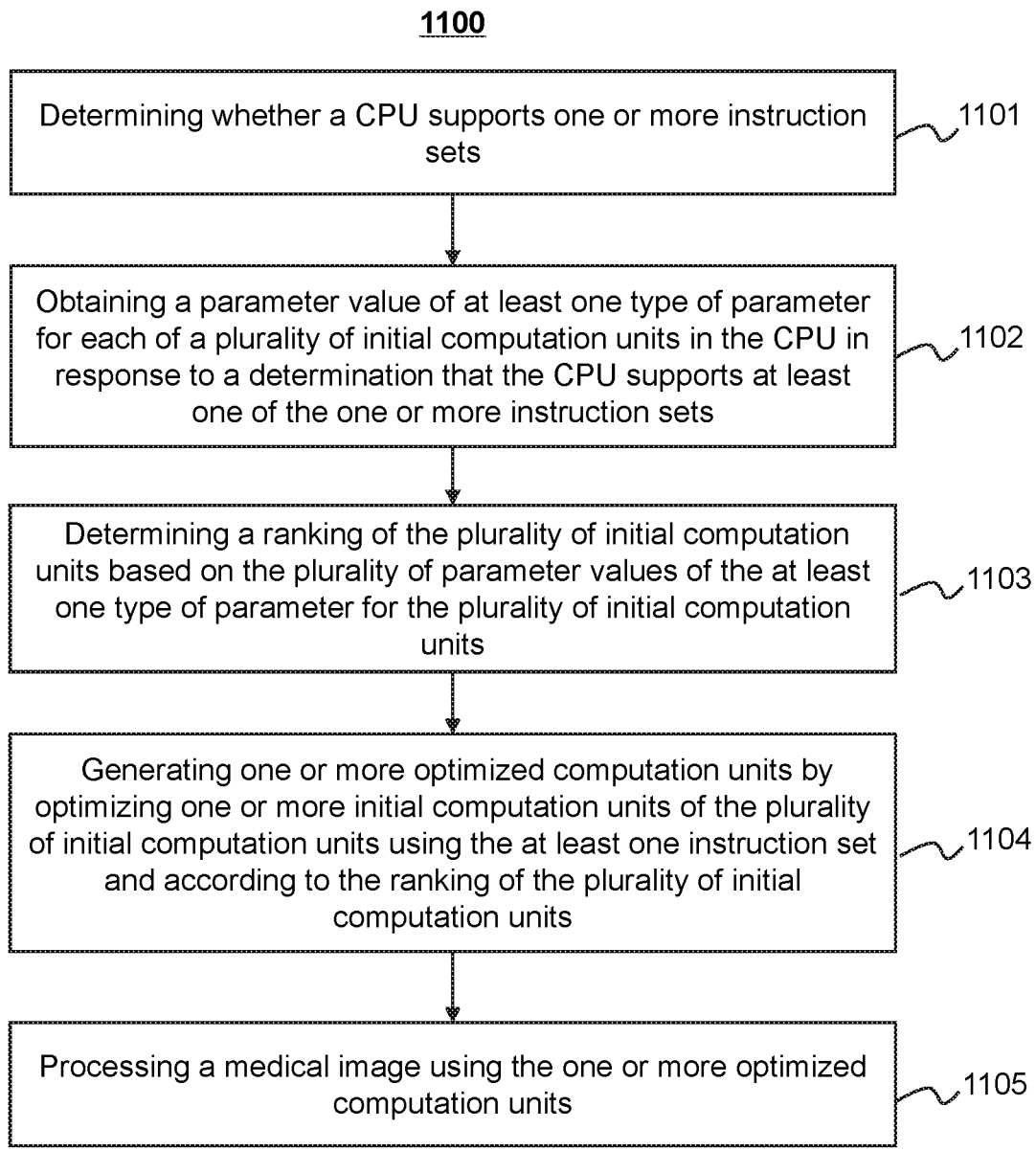
FIG. 11 is a flowchart illustrating an exemplary process for processing a medical image according to some embodiments of the present disclosure.

FIG. 11 is a flowchart illustrating an exemplary process for processing a medical image according to some embodiments of the present disclosure. In some embodiments, at least part of process 1100 may be performed by the processing device 140 (implemented in, for example, the computing device 200 shown in FIG. 2). For example, the process 1100 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1101, the processing device 140 (e.g., the determination unit 510) may determine whether a CPU supports one or more instruction sets.

As used herein, a CPU may refer to an electronic circuitry within a computer (or computing device) that may execute instructions of a computer program by performing one or more basic arithmetic, logical, control and input/output (I/O) operations specified by the instructions. The CPU may function as a computing core and a control core of a computer. As used herein, an instruction set may refer to a group of commands in machine language that can be recognized and performed by a CPU. In some embodiments, the instruction set may be integrated or stored in the CPU. The instruction set may perform mathematical operations such as addition, subtraction, multiplication, and division on one or more initial computation units in the CPU to realize the optimization of the initial computation unit(s). The instruction set may include an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, a virtual machine extension (VMX) instruction set, or the like, or any combination thereof.

In some embodiments, one or more instruction sets may be preset in one or more components of the image processing system 100. The image processing system 100 may automatically determine whether the CPU supports the one or more instruction sets when it starts up. In some embodiments, the processing device 140 may select a target instruction set from the one or more instruction sets that the CPU supports for optimizing one or more initial computation units of a processing program. In some embodiments, the processing device 140 may select a target instruction set based on performances of the one or more instruction sets according to different optimization purposes. For example, the processing device 140 may select a target instruction set that may optimize operation time of an initial computation unit. As another example, the processing device 140 may select a target instruction set that may optimize operational power consumption of an initial computation unit. More descriptions of the determination of the one or more instruction sets may be found elsewhere in the present disclosure (e.g., FIG. 7 and descriptions thereof).

In 1102, the processing device 140 (e.g., the determination unit 510) may obtain a parameter value of at least one type of parameter for each of a plurality of initial computation units in the CPU in response to a determination that the CPU supports at least one of the one or more instruction sets.

In some embodiments, a type of parameter for an initial computation unit may include an operation time of the initial computation unit, a resource capacity of the CPU occupied by the initial computation unit, a count of instructions included in the initial computation unit, or the like, or any combination thereof. More descriptions of the type of parameter for an initial computation unit may be found elsewhere in the present disclosure (e.g., FIG. 7 and descriptions thereof).

In some embodiments, the processing device 140 may obtain a parameter value of a type of parameter for each of the plurality of initial computation units. In some embodiments, a parameter value of a type of parameter for an initial computation unit may indicate an operational performance of the initial computation unit. For example, the processing device 140 may obtain a parameter value of the operation time for each of the plurality of initial computation units. An initial computation unit with a relatively long operation time may lead to a relatively slow operating speed of the CPU. As another example, the processing device 140 may obtain a parameter value of the resource capacity of the CPU occupied by each of the plurality of initial computation units. An initial computation unit that occupies more resource capacities of the CPU may lead to a relatively slow operating speed of the CPU. As still another example, the processing device 140 may obtain a parameter value of the count of instructions included in each of the plurality of initial computation units. An initial computation unit with a relatively large count of instructions may have more abundant arithmetic logic, which may lead to a relatively slow operating speed and/or a relatively long operation time of the CPU.

In some embodiments, the processing device 140 may determine the parameter value of each type of parameter for each of the plurality of initial computation units by executing all instructions in the initial computation unit for a plurality of times. Merely for illustration purpose, if the processing device 140 executes all instructions in an initial computation unit A for three times, and the parameter values of the operation time for the initial computation unit A are t1, t2, and t3, respectively. In this situation, the processing device 140 may determine that the parameter value of the operation time for the initial computation unit A is (t1+t2+t3)/3.

In 1103, the processing device 140 (e.g., the ranking unit 530) may determine a ranking of the plurality of initial computation units based on the plurality of parameter values of the at least one type of parameter for the plurality of initial computation units.

In some embodiments, the processing device 140 may rank the plurality of initial computation units based on a plurality of parameter values of a specific type of parameter for the plurality of initial computation units. In some embodiments, an initial computation unit having a parameter value of a type of parameter that may lead to a relatively slow operating speed of the CPU may have to a relatively high ranking. For example, an initial computation unit with a relatively long operation time may lead to a relatively slow operating speed of the CPU. Accordingly, the processing device 140 may rank the plurality of initial computation units according to their operation times in a descending order.

In some embodiments, the processing device 140 may rank the plurality of initial computation units based on a plurality of parameter values of multiple types of parameters for the plurality of initial computation units. For example, for each of the plurality of initial computation units, the processing device 140 may determine a score for each type of the multiple types of parameters associated with the each of the plurality of initial computation units. Merely for illustration purpose, if a processing program includes an initial computation unit A, an initial computation unit B, an initial computation unit C, and the parameter values of the operation time for the initial computation unit A, the initial computation unit B, and the initial computation unit C are a, b, and c, respectively, then the processing device 140 may determine that the score for the operation time associated with the initial computation unit A is Pa (i.e., Pa=a/(a+b+c)), the score for the operation time associated with the initial computation unit B is Pb (i.e., Pb=b/(a+b+c)), the score for the operation time associated with the initial computation unit C is Pc (i.e., Pc=c/(a+b+c)), wherein Pa+Pb+Pc=1. Similarly, the processing device 140 may determine that the scores for the resource capacities of the CPU occupied by the initial computation unit A, the initial computation unit B, and the initial computation unit C are Qa, Qb, and Qc, respectively. The processing device 140 may determine that the scores for the counts of instructions included in the initial computation unit A, the initial computation unit B, and the initial computation unit C are Ra, Rb, and Rc, respectively. The processing device 140 may also determine a total score for the each of the plurality of initial computation units based on the score for the each type of the multiple types of parameters associated with the each of the plurality of initial computation units. Merely for illustration purpose, if the score for the operation time associated with the initial computation unit A is Pa, the score for the resource capacity of the CPU occupied by the initial computation unit A is Qa, the score for the count of instructions included in the initial computation unit A is Ra, a weight corresponding to the operation time is W1, a weight corresponding to the resource capacity of the CPU occupied by the initial computation unit A is W2, and a weight corresponding to the count of instructions included in the initial computation unit A is W3, then the processing device 140 may determine that the total score for the initial computation unit A is PA=(Pa×W1+Qa×W2+Ra×W3)/(W1+W2+W3). Similarly, the processing device 140 may determine the total score for the initial computation unit B (e.g., PB=(Pb×W1+Qb×W2+Rb×W3)/(W1+W2+W3)), and the total score for the initial computation unit C (e.g., PC=(Pc×W1+Qc×W2+Rc×W3)/(W1+W2+W3)). The processing device 140 may further determine the ranking of the plurality of initial computation units based on the total scores of the plurality of initial computation units. Merely for illustration purpose, if PA>PB>PC, the processing device 140 may determine the ranking of the initial computation units as: initial computation unit A, initial computation unit B, initial computation unit C. Accordingly, the processing device 140 may first optimize the initial computation unit A. In some embodiments, the processing device 140 may then optimize the initial computation unit B. In some embodiments, the processing device 140 may further optimize the initial computation unit C.

In 1104, the processing device 140 (e.g., the optimization unit 540) may generate one or more optimized computation units by optimizing one or more initial computation units of the plurality of initial computation units using the at least one instruction set and according to the ranking of the plurality of initial computation units.

In some embodiments, the processing device 140 may optimize the one or more initial computation units of the plurality of initial computation units based on the ranking of the plurality of initial computation units. In some embodiments, the processing device 140 may determine an expected total operation time of the processing program. The processing device 140 may obtain a parameter value of the operation time for each of the plurality of initial computation units as described in connection with operation 1102. The processing device 140 may determine a ranking of the plurality of initial computation units based on the plurality of parameter values of the operation time for the plurality of initial computation units as described in connection with operation 1103. For example, the processing device 140 may rank the plurality of initial computation units according to their operation times in a descending order. The optimization of an initial computation with a relatively long operation time may improve the operating speed of the CPU more effectively. Accordingly, the processing device 140 may optimize one or more of the plurality of initial computation units in sequence according to the ranking of the plurality of initial computation units. After optimizing an initial computation unit of the plurality of initial computation units, the processing device 140 may determine an estimated total operation time of the processing program based on the operation times associated with the one or more optimized computation units and the rest of the plurality of initial computation units. The processing device 140 may determine whether the estimated total operation time is less than or equal to the expected total operation time. In response to a determination that the estimated total operation time is less than or equal to the expected total operation time, the processing device 140 may terminate the optimizing operation, so as to save time and system resource. In response to a determination that the estimated total operation time is larger than the expected total operation time, the processing device 140 may determine whether the optimizing operation has been performed on all of the plurality of initial computation units. In response to a determination that the optimizing operation has not been performed on all of the plurality of initial computation units, the processing device 140 may further optimize another initial computation unit in the rest of the plurality of initial computation units according to the ranking of rest of the plurality of initial computation units. For example, the processing device 140 may optimize an initial computation unit with a highest ranking in the rest of the plurality of initial computation units. In response to a determination that the optimizing operation has been performed on all of the plurality of initial computation units and/or the estimated total operation time is larger than the expected total operation time, the processing device 140 may generate, in the processing program, an instruction for adding one or more threads or invoking multi threads for processing the medical image in the CPU. More descriptions of the generation of the one or more optimized computation units may be found elsewhere in the present disclosure (e.g., FIGS. 8 and 9 and descriptions thereof).

Accordingly, the operating speed of the CPU may be improved effectively and quickly, and the one or more optimized computation units (i.e., an optimized processing program) may be used to process a medical image. Furthermore, it is possible to use only CPU (without using GPU) to process the medical image while ensuring the operating speed of the CPU.

In 1105, the processing device 140 (e.g., the processing unit 550) may process a medical image using the one or more optimized computation units.

In some embodiments, the processing device 140 may determine an (optimized) processing program based on the one or more optimized computation units. The processing device 140 may process the medical image using the (optimized) processing program. More descriptions for processing a medical image may be found elsewhere in the present disclosure (e.g., FIG. 6 and descriptions thereof).

The image processing method described in the present disclosure may include determining whether a CPU supports one or more instruction sets. The method may also include determining a ranking of a plurality of initial computation units in response to a determination that the CPU supports at least one of the one or more instruction sets. The method may further include optimizing one or more initial computation units of the plurality of initial computation units using the at least one instruction set and/or according to the ranking of the plurality of initial computation units. The method may still further include processing a medical image using the one or more optimized computation units. Therefore, it is possible to save costs by replacing a GPU with a CPU in processing a medical image, while ensuring the operating speed of the CPU.

It should be noted that the above description of the process 1100 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure.

Figure 12:
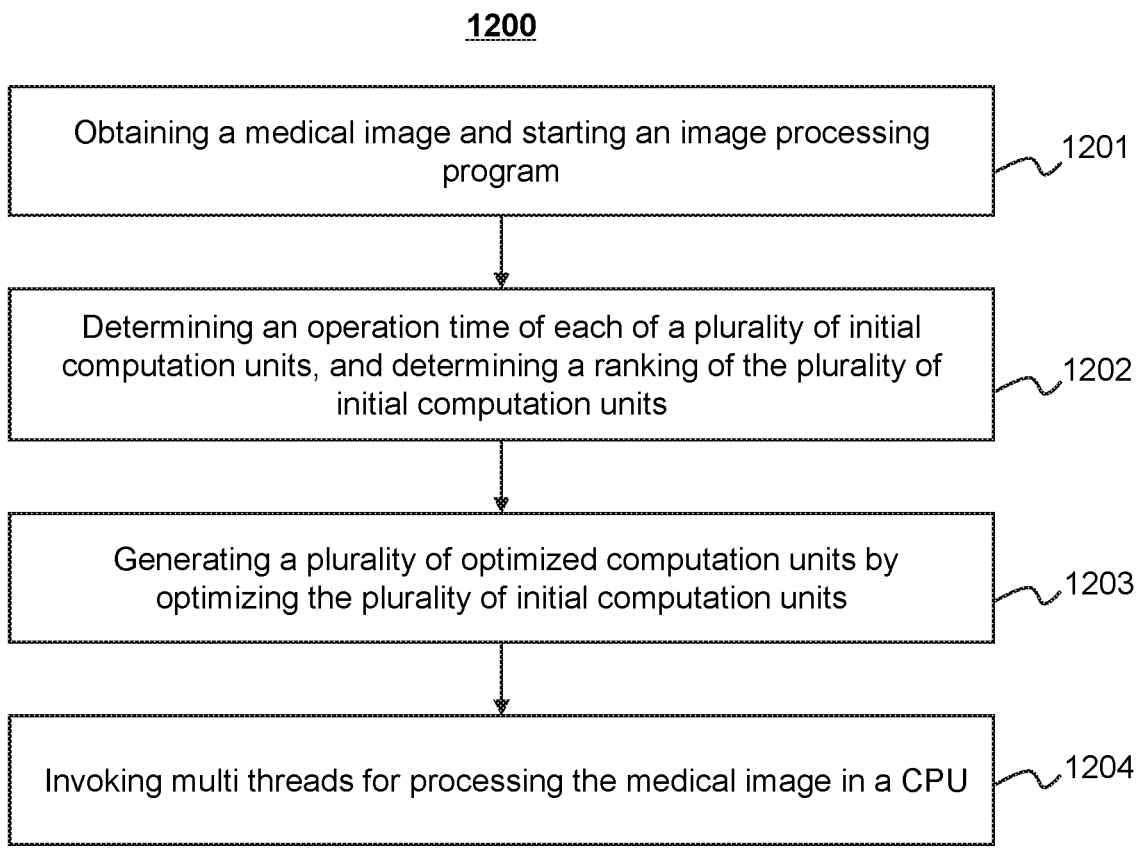
FIG. 12 is a flowchart illustrating an exemplary process for processing a medical image according to some embodiments of the present disclosure.

FIG. 12 is a flowchart illustrating an exemplary process for processing a medical image according to some embodiments of the present disclosure. In some embodiments, at least part of process 1200 may be performed by the processing device 140 (implemented in, for example, the computing device 200 shown in FIG. 2). For example, the process 1200 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1201, the processing device 140 (e.g., the obtaining unit 520) may obtain a medical image and start an image processing program. In some embodiments, the processing device 140 may obtain the image from one or more components (e.g., the scanner 110, the terminal 140, and the storage device 150) of the image processing system 100 or an external storage device via the network 120.

In some embodiments, the image may be a medical image. For example, the image may be a CT image, an MRI image, a PET-CT image, an MRI-CT image, or the like. In some embodiments, the image may be a two-dimensional (2D) image, a three-dimensional (3D) image, a four-dimensional (4D) image, or the like. In some embodiments, the scanner 110 may obtain projection data via scanning a subject or a part of the subject. The processing device 140 may generate the image based on projection data generated by the scanner 110. In some embodiments, the processing device 140 may display the image on an interface of the display module 410.

In some embodiments, the image processing program may include an image segmentation program, an image classification program, an image recognition program, an image binarization program, or the like, or any combination thereof. In some embodiments, the image processing program may include a plurality of initial computation units as described elsewhere in the present disclosure (e.g., FIG. 7 and descriptions thereof).

In some embodiments, one or more instruction sets may be preset in one or more components of the image processing system 100. In some embodiments, the image processing system 100 may automatically determine whether the CPU supports the one or more instruction sets when the image processing program starts up. In some embodiments, the processing device 140 may select a target instruction set from the one or more instruction sets that the CPU supports for optimizing one or more initial computation units of the image processing program.

In 1202, the processing device 140 (e.g., the determination unit 510) may determine an operation time of each of a plurality of initial computation units, and determining a ranking of the plurality of initial computation units.

In some embodiments, the processing device 140 may rank the plurality of initial computation units based on a plurality of parameter values of a specific type of parameter for the plurality of initial computation units. For example, the processing device 140 may rank the plurality of initial computation units according to their operation times in a descending order. Merely for illustration purpose, if a processing program includes an initial computation unit A having an operation time of 10 ms, an initial computation unit B having an operation time of 20 ms, and an initial computation unit C having an operation time of 30 ms, then the processing device 140 may determine the ranking of the initial computation units as: initial computation unit C, initial computation unit B, initial computation unit A.

In 1203, the processing device 140 (e.g., the optimization unit 540) may generate a plurality of optimized computation units by optimizing the plurality of initial computation units.

In some embodiments, the processing device 140 may select one or more initial computation units from the plurality of initial computation units based on an expected total operation time and the operation time associated with each of the plurality of initial computation units, according to the ranking of the plurality of initial computation units. In some embodiments, the processing device 140 may select the one or more computation units based on an expected minimum operation time associated with each of the plurality of initial computation units, and the expected total operation time, according to the ranking of the plurality of initial computation units. Merely for illustration purpose, if a processing program includes an initial computation unit A having an operation time of 10 ms, an initial computation unit B having an operation time of 20 ms, an initial computation unit C having an operation time of 30 ms, then the processing device 140 may determine the ranking of the initial computation units as: initial computation unit C, initial computation unit B, initial computation unit A. If the minimum operation times associated with the initial computation unit A, the initial computation unit B, and the initial computation unit C are determined as: 5 ms, 10 ms, and 15 ms, respectively, and the expected total operation time is 35 ms, then the processing device 140 may select the initial computation unit C and the initial computation unit B for optimization. That is, the processing device 140 may first optimize the initial computation unit C, and then optimize the initial computation unit B. Accordingly, an estimated total operation time of the processing program (i.e., 15 ms+10 ms+10 ms=35 ms) after optimization may be no larger than the expected total operation time of the processing program, which means the optimization purpose can be achieved without optimizing the initial computation unit A. Therefore, the processing device 140 may select the initial computation unit C and the initial computation unit B for optimization to achieve the optimization purpose.

In 1204, the processing device 140 (e.g., the optimization unit 540) may invoke multi threads for processing the medical image in CPU.

In some embodiments, the processing device 140 may generate, in the image processing program, an instruction for adding one or more threads or invoking multi threads for processing the medical image in CPU. Accordingly, the speed of image processing may be improved by adding one or more threads or invoking multi threads for processing the medical image in CPU. The processing device 140 may process the medical image based on the one or more optimized computation units implemented in the CPU (e.g., an optimized processing program). More descriptions for adding one or more threads or invoking multi threads in an image processing program may be found elsewhere in the present disclosure (e.g., FIG. 9 and descriptions thereof).

It should be noted that the above descriptions of the process 600 through 1200 are provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the image processed in process 600 may be a medical image. In some embodiments, the processing of the medical image may be implemented on at least one central processing unit (CPU). In some embodiments, the medical image may be obtained by the at least one CPU. In some embodiments, the at least one CPU may process the medical image using a processing program. In some embodiments, the processing program may include one or more optimized computation units. In some embodiments, the one or more optimized computation units may be optimized by an instruction set. In some embodiments, the instruction set may be supported by the at least one CPU. In some embodiments, the instruction set may be configured to optimize an operation time of the processing program, a resource of the at least one CPU occupied by the processing program, and/or a count of instructions included in the processing program. In some embodiments, the instruction set may include an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, a virtual machine extension (VMX) instruction set, or the like, or a combination thereof.

In some embodiments, the at least one CPU may include at least two cores corresponding to at least two threads respectively. In some embodiments, the medical image may be processed by implementing the processing program using the at least two threads.

In some embodiments, the medical image may be generated by a single modality imaging device or a multi-modality imaging device. In some embodiments, the single modality imaging device may include a CT imaging device, an MR imaging device, a PET imaging device, a CBCT imaging device, an SPET imaging device, an XR imaging device, an FFDM imaging device, or a DBT imaging device. In some embodiments, the multi-modality imaging device may include a PET-MR imaging device, a PET-CT imaging device, or an SPET-CT imaging device, or the like, or a combination thereof.

More descriptions of the processing of the medical image and/or optimization of the processing program may be found elsewhere in the present disclosure (e.g., FIGS. 6-12 and descriptions thereof).

It should be noted that the above description of the process 600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device including a storage device and at least one central processing unit (CPU) for processing a medical image, the method comprising:
obtaining the medical image; and
processing the medical image using a processing program, the processing program including one or more optimized computation units, wherein each of the one or more optimized computation units is obtained by optimizing a corresponding initial computation unit of the processing program based on a total score for the corresponding initial computation unit, using an instruction set supported by the at least one CPU, the total score for the corresponding initial computation unit being determined based on a score for each type of at least two types of parameters associated with the corresponding initial computation unit, the instruction set being configured to optimize at least one of:
an operation time of the processing program,
a resource of the at least one CPU occupied by the processing program, or
a count of instructions included in the processing program.

2. The method of claim 1, wherein the instruction set includes at least one of an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, or a virtual machine extension (VMX) instruction set.

3. The method of claim 1, wherein the at least one CPU includes at least two cores corresponding to at least two threads respectively, and wherein processing the medical image using a processing program comprises:
processing the medical image by implementing the processing program using the at least two threads.

4. The method of claim 1, wherein the medical image is generated by a single modality imaging device or a multi-modality imaging device.

5. The method of claim 4, wherein the single modality imaging device includes a CT imaging device, an MR imaging device, a PET imaging device, a CBCT imaging device, an SPET imaging device, an XR imaging device, an FFDM imaging device, or a DBT imaging device.

6. A method implemented on a computing device including a storage device and at least one central processing unit (CPU) for processing an image, the method comprising:
obtaining an image; and
processing the image using a processing program, the processing program including one or more optimized computation units;
wherein the one or more optimized computation units are obtained according to a process, the process including:
obtaining a plurality of initial computation units of the processing program, each of the plurality of initial computation units having at least two types of parameters indicating operational performances of the each of the plurality of initial computation units, each of the at least two types of parameters for each of the plurality of initial computation units having a parameter value;
determining at least one instruction set that the at least one CPU supports;
determining-a parameter values of the at least two types of parameters for each of the plurality of initial computation units;
determining a total score for each of the plurality of initial computation units based on a score for each type of the at least two types of parameters associated with the each of the plurality of initial computation units; and
generating each of the one or more optimized computation units by optimizing a corresponding initial computation unit of the plurality of initial computation units using the at least one instruction set, based on the total scores for the plurality of initial computation units.

7. The method of claim 6, wherein the instruction set includes at least one of an advanced vector extensions (AVX) instruction set, an AVX2 instruction set, AVX-512, a streaming single instruction multiple data extensions (SSE) instruction set, an SSE2 instruction set, an SSE3 or SSSE3 instruction set, an SSE4 or SSE4A instruction set, an SSE4.5 or SSE4.2 instruction set, a multi-media extension (MMX) instruction set, an x86 or x86-64 instruction set, a 3D-Now instruction set, an extended memory 64 technology (EM64T) instruction set, or a virtual machine extension (VMX) instruction set.

8. The method of claim 6, wherein the at least two types of parameters indicating the operational performances of the each of the plurality of initial computation units includes an operation time of the each of the plurality of initial computation units.

9. The method of claim 6, further comprising:
determining a ranking of an optimization priority of the plurality of initial computation units based on the total scores for the plurality of initial computation units.

10. The method of claim 9, wherein generating each of the one or more optimized computation units by optimizing a corresponding initial computation unit of the plurality of initial computation units using the at least one instruction set comprises:
generating the each of the one or more optimized computation units by optimizing the corresponding initial computation unit of the plurality of initial computation units using the at least one instruction set and according to the ranking of the optimization priority of the plurality of initial computation units.

11. The method of claim 10, wherein the generating the each of the one or more optimized computation units comprises:
determining an expected total operation time of the processing program;
selecting one or more initial computation units from the plurality of initial computation units based on the expected total operation time and the operation time associated with each of the plurality of initial computation units, according to the ranking of the optimization priority of the plurality of initial computation units; and
optimizing the each of the one or more initial computation units using the at least one instruction set.

12. The method of claim 10, wherein the generating the each of the one or more optimized computation units comprises:
determining an expected total operation time of the processing program;
after optimizing the corresponding initial computation unit,
determining an estimated total operation time of the processing program based on the operation times associated with the one or more optimized computation units and the rest of the plurality of initial computation units; and
determining whether the estimated total operation time is less than or equal to the expected total operation time.

13. The method of claim 12, wherein the generating the each of the one or more optimized computation units further comprises:
upon determination that the estimated total operation time is less than or equal to the expected total operation time, terminating the optimization of one or more initial computation units of the plurality of initial computation units.

14. The method of claim 12, wherein the generating the each of the one or more optimized computation units further comprises:
upon determination that the estimated total operation time is larger than the expected total operation time,
determining whether the optimizing operation has been performed on all of the plurality of initial computation units.

15. The method of claim 14, wherein the generating the each of the one or more optimized computation units further comprises:
upon determination that the optimizing operation has been performed on all of the plurality of initial computation units,
generating, in the processing program, an instruction for
adding one or more threads for processing the image in the at least one CPU, or
invoking multi threads for processing the image in the at least one CPU.

16. The method of claim 6, wherein the at least two types of parameters indicating the operational performances of the each of the plurality of initial computation units includes two or more of
an operation time of the each of the plurality of initial computation units,
a resource of the at least one CPU occupied by the each of the plurality of initial computation units, and
a count of instructions included in the each of the plurality of initial computation units.

17. A system for processing a medical image, comprising:
at least one storage device including a set of instructions or programs; and
at least one central processing unit (CPU) configured to communicate with the at least one storage device, wherein when executing the set of instructions or programs, the at least one CPU is configured to cause the system to perform operations including:
obtaining the medical image; and
processing the medical image using a processing program, the processing program including one or more optimized computation units, wherein each of the one or more optimized computation units is obtained by optimizing a corresponding initial computation unit of the processing program based on a total score for the corresponding initial computation unit, using an instruction set supported by the at least one CPU, the total score for the corresponding initial computation unit being determined based on a score for each type of at least two types of parameters associated with the corresponding initial computation unit, the instruction set being configured to optimize at least one of:
an operation time of the processing program,
a resource of the at least one CPU occupied by the processing program, or
a count of instructions included in the processing program.

18. The method of claim 6, wherein the determining a total score for each of the plurality of initial computation units based on a score for each type of the at least two types of parameters associated with the each of the plurality of initial computation units comprises:
for each of the plurality of initial computation units,
determining a score for each type of the at least two types of parameters associated with the each of the plurality of initial computation units; and
determining the total score for the each of the plurality of initial computation units based on the score for the each type of the at least two types of parameters associated with the each of the plurality of initial computation units.

19. The method of claim 18, wherein the determining a score for each type of the at least two types of parameters associated with the each of the plurality of initial computation units comprises:
for the each type of the at least two types of parameters,
determining the score for the each type associated with the each of the plurality of initial computation units by normalizing a plurality of parameter values of the each type associated with the plurality of initial computation units.

20. The method of claim 18, wherein the determining the total score for the each of the plurality of initial computation units comprises:
determining the total score for the each of the plurality of initial computation units based on a weighted mean of scores for the at least two types of parameters associated with the each of the plurality of initial computation units.

* * * * *